(12) United States Patent
Limem et al.

(10) Patent No.: US 11,833,027 B2
(45) Date of Patent: Dec. 5, 2023

(54) FULL CONTOUR BREAST IMPLANT

(71) Applicant: Tepha, Inc., Lexington, MA (US)

(72) Inventors: Skander Limem, Melrose, MA (US); Said Rizk, Windham, NH (US); Simon F. Williams, Cambridge, MA (US)

(73) Assignee: Tepha, Inc., Lexington, MA (US)

( * ) Notice: Subject to any disclaimer, the term of this patent is extended or adjusted under 35 U.S.C. 154(b) by 84 days.

(21) Appl. No.: 17/486,879

(22) Filed: Sep. 27, 2021

(65) Prior Publication Data
US 2022/0079741 A1    Mar. 17, 2022

Related U.S. Application Data

(62) Division of application No. 16/262,018, filed on Jan. 30, 2019, now Pat. No. 11,154,393.
(Continued)

(51) Int. Cl.
*A61F 2/12*  (2006.01)
*A61F 2/00*  (2006.01)

(52) U.S. Cl.
CPC ............. *A61F 2/12* (2013.01); *A61F 2/0063* (2013.01); *A61F 2210/0004* (2013.01);
(Continued)

(58) Field of Classification Search
CPC .. A61F 2/12; A61F 2/0063; A61F 2210/0004; A61F 2230/008; A61F 2240/00; A61F 2250/0067
See application file for complete search history.

(56) References Cited

U.S. PATENT DOCUMENTS

| | | |
|---|---|---|
| 2,701,879 A | 2/1955 | Bennett |
| 3,280,818 A | 10/1966 | Pankey et al. |

(Continued)

FOREIGN PATENT DOCUMENTS

| | | |
|---|---|---|
| CA | 2829201 A1 | 9/2012 |
| EP | 1940312 B1 | 7/2009 |

(Continued)

OTHER PUBLICATIONS

Mallucci et al (Journal of Plastic, Reconstructive, and Aesthetic Surgery, "Concepts in aesthetic breast dimensions: Analysis of the ideal breast" (2012) 65, pp. 8-16) (Year: 2012).*
(Continued)

*Primary Examiner* — Keri J Nelson
*Assistant Examiner* — Rebecca Lynee Zimmerman
(74) *Attorney, Agent, or Firm* — Wolf, Greenfield & Sacks, P.C.

(57) ABSTRACT

Full contour absorbable implants for breast surgery redistribute breast volume between the breast's upper and lower poles in exact and desirable ratios. The implants preferably redistribute breast volume so that the upper pole breast volume is 20-40% of the total volume, and the lower pole breast volume is 60-80% of the total volume. The implants are also designed to provide specific curvatures to the poles of the breast, and to angulate the nipple areolar complex slightly skyward so that the patient's nipple is positioned at an angle above the nipple meridian reference line. The implants are designed to be transitory, with sufficient strength retention to allow transition from support of the breast by the implant to support by regenerated host tissue growing in and around the implants, without any significant loss of support during or subsequent to remodeling. The implants may optionally be used with permanent breast implants.

30 Claims, 12 Drawing Sheets

US 11,833,027 B2
Page 2

Related U.S. Application Data

(60) Provisional application No. 62/628,739, filed on Feb. 9, 2018.

(52) U.S. Cl.
CPC ..... *A61F 2230/008* (2013.01); *A61F 2240/00* (2013.01); *A61F 2250/0067* (2013.01)

(56) References Cited

U.S. PATENT DOCUMENTS

| | | |
|---|---|---|
| 3,293,663 A | 12/1966 | Cronin |
| 3,366,975 A | 2/1968 | Pangman |
| 3,934,593 A | 1/1976 | Mellinger |
| 4,372,293 A | 2/1983 | Vijil-Rosales |
| 4,380,569 A | 4/1983 | Shaw |
| 4,388,735 A | 6/1983 | Ionescu et al. |
| 4,773,909 A | 9/1988 | Chaglassian |
| 4,801,299 A | 1/1989 | Brendel et al. |
| 4,863,470 A | 9/1989 | Carter |
| 4,936,858 A | 6/1990 | O'Keeffe |
| 4,960,425 A | 10/1990 | Yan et al. |
| 5,007,929 A | 4/1991 | Quaid |
| 5,011,494 A | 4/1991 | von Recum et al. |
| 5,217,494 A | 6/1993 | Coggins et al. |
| 5,356,429 A | 10/1994 | Seare |
| 5,383,929 A | 1/1995 | Ledergerber |
| 5,480,430 A | 1/1996 | Carlisle et al. |
| 5,500,019 A | 3/1996 | Johnson et al. |
| 5,545,221 A | 8/1996 | Hang-Fu |
| 5,584,884 A | 12/1996 | Pignataro |
| 5,658,328 A | 8/1997 | Johnson |
| 5,658,329 A | 8/1997 | Purkait |
| 5,676,161 A | 10/1997 | Breiner |
| 5,716,404 A | 2/1998 | Vacanti et al. |
| 5,755,611 A | 5/1998 | Noble et al. |
| 5,759,204 A | 6/1998 | Seare |
| 5,902,335 A | 5/1999 | Snyder, Jr. |
| 5,990,378 A | 11/1999 | Ellis |
| 6,074,421 A | 6/2000 | Murphy |
| 6,113,634 A | 9/2000 | Weber-Unger et al. |
| 6,146,418 A | 11/2000 | Berman |
| 6,210,439 B1 | 4/2001 | Firmin et al. |
| 6,328,765 B1 | 12/2001 | Hardwick et al. |
| 6,368,541 B1 | 4/2002 | Pajotin et al. |
| 6,371,831 B1 | 4/2002 | Dodge |
| 6,544,287 B1 | 4/2003 | Johnson et al. |
| 6,599,323 B2 | 7/2003 | Melican et al. |
| 6,682,559 B2 | 1/2004 | Myers et al. |
| 6,723,133 B1 | 4/2004 | Pajotin |
| 6,740,122 B1 | 5/2004 | Pajotin |
| 6,913,626 B2 | 7/2005 | McGhan |
| 7,081,135 B2 | 7/2006 | Smith et al. |
| D539,506 S | 4/2007 | Valentin |
| 7,476,249 B2 | 1/2009 | Frank |
| 7,520,896 B2 | 4/2009 | Benslimane |
| 7,670,372 B2 | 3/2010 | Shfaram et al. |
| 7,875,074 B2 | 1/2011 | Chen et al. |
| 7,998,202 B2 | 8/2011 | Lesh |
| 8,007,531 B2 | 8/2011 | Frank |
| 8,034,270 B2 | 10/2011 | Martin et al. |
| 8,043,373 B2 | 10/2011 | Schuessler et al. |
| 8,101,116 B2 | 1/2012 | Lindh, Sr. et al. |
| 8,211,173 B2 | 7/2012 | Keller et al. |
| 8,377,127 B2 | 2/2013 | Schuessler |
| 8,506,582 B2 | 8/2013 | Kammerer et al. |
| 8,728,159 B2 | 5/2014 | Kim |
| 8,778,020 B2 | 7/2014 | Gregg et al. |
| 8,858,629 B2 | 10/2014 | Moses et al. |
| 8,911,765 B2 | 12/2014 | Moses et al. |
| 8,936,504 B2 | 1/2015 | Deal et al. |
| 8,986,377 B2 | 3/2015 | Richter et al. |
| 9,277,986 B2 | 3/2016 | Moses et al. |
| 9,474,598 B2 | 10/2016 | Gregg et al. |
| 9,532,867 B2 | 1/2017 | Felix et al. |
| 9,555,155 B2 | 1/2017 | Ganatra et al. |
| 9,585,744 B2 | 3/2017 | Moses et al. |
| 9,603,698 B2 | 3/2017 | Kerr et al. |
| 9,636,211 B2 | 5/2017 | Felix et al. |
| 9,655,715 B2 | 5/2017 | Limem et al. |
| 9,700,411 B2 | 7/2017 | Klima et al. |
| 9,707,073 B2 | 7/2017 | Al-Jasim |
| 9,713,350 B1 | 7/2017 | Colburn |
| 9,713,524 B2 | 7/2017 | Glicksman |
| D799,152 S | 10/2017 | Brownell et al. |
| D803,401 S | 11/2017 | Limem et al. |
| D816,220 S | 4/2018 | Limem et al. |
| D816,221 S | 4/2018 | Limem et al. |
| 10,028,818 B2 | 7/2018 | Felix et al. |
| 10,052,192 B2 | 8/2018 | Schuessler et al. |
| 10,058,417 B2 | 8/2018 | Limem et al. |
| D836,778 S | 12/2018 | Limem et al. |
| 10,258,460 B2 | 4/2019 | Moses et al. |
| 10,363,127 B2 | 7/2019 | Mlodinow et al. |
| D856,517 S | 8/2019 | Spiegel et al. |
| D857,895 S | 8/2019 | Limem et al. |
| 10,405,969 B2 | 9/2019 | Bertoli et al. |
| 10,449,034 B2 | 10/2019 | Bowley et al. |
| D870,289 S | 12/2019 | Limem et al. |
| 10,568,728 B2 | 2/2020 | Felix et al. |
| 10,595,986 B2 | 3/2020 | Rehnke |
| D888,244 S | 6/2020 | Limem et al. |
| 10,695,165 B2 | 6/2020 | Shetty et al. |
| D889,654 S | 7/2020 | Limem et al. |
| D889,655 S | 7/2020 | Limem et al. |
| 10,722,345 B2 | 7/2020 | Limem et al. |
| D892,329 S | 8/2020 | Limem et al. |
| D894,393 S | 8/2020 | Limem et al. |
| D896,383 S | 9/2020 | Schuessler et al. |
| 10,765,507 B2 | 9/2020 | Moses et al. |
| D926,984 S | 8/2021 | Schuessler et al. |
| D927,690 S | 8/2021 | Limem et al. |
| 11,154,393 B2 | 10/2021 | Limem et al. |
| D956,977 S | 7/2022 | Limem et al. |
| 2002/0022883 A1 | 2/2002 | Burg |
| 2002/0143396 A1 | 10/2002 | Falcon et al. |
| 2002/0165596 A1 | 11/2002 | Wilson |
| 2003/0195620 A1 | 10/2003 | Huynh et al. |
| 2003/0207649 A1 | 11/2003 | Reeder |
| 2003/0212461 A1 | 11/2003 | Vadurro et al. |
| 2003/0212462 A1 | 11/2003 | Gryska et al. |
| 2004/0225352 A1 | 11/2004 | Osborne et al. |
| 2005/0027348 A1 | 2/2005 | Case et al. |
| 2006/0167338 A1 | 7/2006 | Shfaram et al. |
| 2006/0211334 A1 | 9/2006 | Smith |
| 2007/0055371 A1 | 3/2007 | Laghi |
| 2007/0088434 A1 | 4/2007 | Frank |
| 2007/0135929 A1 | 6/2007 | Williams et al. |
| 2007/0196421 A1 | 8/2007 | Hunter et al. |
| 2007/0198085 A1 | 8/2007 | Benslimane |
| 2008/0027273 A1 | 1/2008 | Gutterman |
| 2008/0082113 A1 | 4/2008 | Bishop et al. |
| 2008/0097601 A1 | 4/2008 | Codori-Hurff et al. |
| 2008/0128315 A1 | 6/2008 | Buevich et al. |
| 2008/0154366 A1 | 6/2008 | Frank |
| 2008/0241212 A1 | 10/2008 | Moses et al. |
| 2009/0082864 A1 | 3/2009 | Chen et al. |
| 2009/0240342 A1 | 9/2009 | Lindh, Sr. et al. |
| 2009/0248071 A1 | 10/2009 | Saint et al. |
| 2010/0021738 A1 | 1/2010 | Maida et al. |
| 2010/0023120 A1 | 1/2010 | Holecek et al. |
| 2010/0030015 A1 | 2/2010 | Delorme et al. |
| 2010/0042211 A1 | 2/2010 | Epps et al. |
| 2010/0137679 A1 | 6/2010 | Lashinski et al. |
| 2010/0191330 A1* | 7/2010 | Lauryssen .................. A61F 2/12 623/8 |
| 2010/0204791 A1 | 8/2010 | Shfaram et al. |
| 2010/0217388 A1 | 8/2010 | Cohen et al. |
| 2010/0249924 A1 | 9/2010 | Powell et al. |
| 2010/0249947 A1 | 9/2010 | Lesh et al. |
| 2010/0305696 A1 | 12/2010 | Mao et al. |
| 2010/0331612 A1 | 12/2010 | Lashinski et al. |
| 2011/0009960 A1 | 1/2011 | Altman et al. |
| 2011/0022171 A1 | 1/2011 | Richter et al. |
| 2011/0257665 A1 | 10/2011 | Mortarino |

(56) References Cited

U.S. PATENT DOCUMENTS

| | | |
|---|---|---|
| 2011/0264213 A1 | 10/2011 | DeMiranda |
| 2011/0276122 A1 | 11/2011 | Schlick et al. |
| 2011/0301706 A1 | 12/2011 | Brooks et al. |
| 2012/0004723 A1 | 1/2012 | Mortarino et al. |
| 2012/0021738 A1 | 1/2012 | Koo et al. |
| 2012/0022646 A1 | 1/2012 | Mortarino et al. |
| 2012/0158134 A1 | 6/2012 | Codori-Hurff et al. |
| 2012/0185041 A1 | 7/2012 | Mortarino et al. |
| 2012/0221105 A1 | 8/2012 | Altman et al. |
| 2012/0226352 A1 | 9/2012 | Becker |
| 2012/0232653 A1 | 9/2012 | Saint et al. |
| 2012/0266348 A1 | 10/2012 | Meginnis |
| 2012/0283826 A1 | 11/2012 | Moses et al. |
| 2013/0066423 A1 | 3/2013 | Bishop et al. |
| 2013/0103149 A1 | 4/2013 | Altman et al. |
| 2013/0116778 A1 | 5/2013 | Gregg et al. |
| 2013/0178699 A1 | 7/2013 | Saint et al. |
| 2013/0178875 A1 | 7/2013 | Horton et al. |
| 2013/0253645 A1 | 9/2013 | Kerr et al. |
| 2013/0304098 A1 | 11/2013 | Mortarino |
| 2014/0017284 A1 | 1/2014 | Yang et al. |
| 2014/0046442 A1 | 2/2014 | Guterman |
| 2014/0081398 A1 | 3/2014 | Mejia et al. |
| 2014/0135925 A1 | 5/2014 | Brooks et al. |
| 2014/0163696 A1 | 6/2014 | Lesh et al. |
| 2014/0200396 A1 | 7/2014 | Lashinski et al. |
| 2014/0222146 A1 | 8/2014 | Moses et al. |
| 2014/0222161 A1 | 8/2014 | Mathisen |
| 2014/0257482 A1 | 9/2014 | Ward et al. |
| 2014/0276993 A1 | 9/2014 | Reilly et al. |
| 2014/0276997 A1 | 9/2014 | Harrah et al. |
| 2015/0012089 A1 | 1/2015 | Shetty et al. |
| 2015/0018946 A1 | 1/2015 | Guterman |
| 2015/0056131 A1 | 2/2015 | Bernasconi et al. |
| 2015/0081000 A1 | 3/2015 | Hossainy et al. |
| 2015/0112434 A1 | 4/2015 | Felix et al. |
| 2015/0134043 A1 | 5/2015 | Irwin et al. |
| 2015/0223928 A1* | 8/2015 | Limem ............... B29C 48/0022 623/8 |
| 2015/0272722 A1 | 10/2015 | Davila et al. |
| 2015/0351889 A1 | 12/2015 | Reddy et al. |
| 2015/0351891 A1 | 12/2015 | Moses et al. |
| 2015/0351899 A1 | 12/2015 | Mortarino |
| 2015/0351900 A1 | 12/2015 | Glicksman |
| 2016/0022416 A1 | 1/2016 | Felix et al. |
| 2016/0038269 A1 | 2/2016 | Altman et al. |
| 2016/0106538 A1 | 4/2016 | Mitra et al. |
| 2016/0151062 A1 | 6/2016 | Bachrach |
| 2016/0151138 A1 | 6/2016 | Guterman et al. |
| 2016/0166727 A1 | 6/2016 | Ganatra et al. |
| 2016/0256268 A1 | 9/2016 | Dakin |
| 2016/0296329 A1 | 10/2016 | Alkhatib et al. |
| 2016/0310262 A1 | 10/2016 | Doucet et al. |
| 2017/0014226 A1 | 1/2017 | Fenaroli |
| 2017/0065403 A1 | 3/2017 | Al-Jasim |
| 2017/0143475 A1 | 5/2017 | Moses et al. |
| 2017/0196672 A1 | 7/2017 | Guterman |
| 2017/0216009 A1 | 8/2017 | Felix et al. |
| 2017/0216018 A1 | 8/2017 | Limem et al. |
| 2017/0224471 A1 | 8/2017 | Rehnke |
| 2018/0055624 A1 | 3/2018 | Barere et al. |
| 2018/0303599 A1* | 10/2018 | Al-Jasim ................ B29C 41/14 |
| 2018/0325644 A1 | 11/2018 | Felix et al. |
| 2019/0216595 A1 | 7/2019 | Moses et al. |
| 2019/0247180 A1 | 8/2019 | Limem et al. |
| 2019/0254807 A1 | 8/2019 | Limem et al. |
| 2020/0085526 A1 | 3/2020 | Schuessler et al. |
| 2020/0100892 A1 | 4/2020 | Limem et al. |
| 2020/0261202 A1 | 8/2020 | Mathisen et al. |
| 2020/0276006 A1 | 9/2020 | Felix et al. |
| 2020/0360129 A1 | 11/2020 | Moses et al. |
| 2020/0397554 A1 | 12/2020 | Epps et al. |
| 2020/0405473 A1 | 12/2020 | Nanni |
| 2021/0069374 A1 | 3/2021 | Brennan et al. |
| 2021/0153997 A1 | 5/2021 | Limem et al. |
| 2021/0251738 A1 | 8/2021 | Young |
| 2022/0079742 A1 | 3/2022 | Limem et al. |
| 2022/0362001 A1 | 11/2022 | Felix et al. |

FOREIGN PATENT DOCUMENTS

| | | |
|---|---|---|
| EP | 2903563 A1 | 8/2015 |
| EP | 2903563 B1 | 11/2017 |
| EP | 2190382 B1 | 10/2018 |
| JP | 2004-130118 A | 4/2004 |
| JP | 4296399 B2 | 7/2009 |
| WO | WO 2004/096098 A1 | 11/2004 |
| WO | WO 2006/117622 A1 | 11/2006 |
| WO | WO 2007/004214 A3 | 1/2007 |
| WO | WO 2009/001293 A1 | 12/2008 |
| WO | WO 2009/050706 A2 | 4/2009 |
| WO | WO 2011/119742 A2 | 9/2011 |
| WO | WO 2012/012215 A2 | 1/2012 |
| WO | WO 2012/122215 A2 | 9/2012 |
| WO | WO 2014/041577 A1 | 3/2014 |
| WO | WO 2015/006737 A1 | 1/2015 |
| WO | WO 2019/094861 A1 | 5/2019 |
| WO | WO 2019/119060 A1 | 6/2019 |
| WO | WO 2019/175911 A2 | 9/2019 |
| WO | WO 2019/243599 A1 | 12/2019 |
| WO | WO 2020/070694 A1 | 4/2020 |
| WO | WO 2020/072349 A1 | 4/2020 |
| WO | WO 2020/242694 A1 | 12/2020 |
| WO | WO 2021/015976 A1 | 1/2021 |
| WO | WO 2021/024284 A1 | 2/2021 |
| WO | WO 2021/063850 A1 | 4/2021 |
| WO | WO 2021/063851 A1 | 4/2021 |

OTHER PUBLICATIONS

International Search Report and Written Opinion dated Apr. 23, 2019 in connection with International Application No. PCT/US2019/015849.
International Preliminary Report on Patentability dated Aug. 20, 2020 in connection with International Application No. PCT/US2019/015849.
O'Shaughnessy, Evolution and update on current devices for prosthetic breast reconstruction. Gland Surg. Apr. 2015; 4(2):97-110.
U.S. Appl. No. 17/871,155, filed Jul. 22, 2022, Felix et al.
EP 19869949.8, May 31, 2022, Extended European Search Report.
U.S. Appl. No. 16/587,903, filed Sep. 30, 2019, Limem et al.
U.S. Appl. No. 16/797,960, filed Feb. 21, 2020, Felix et al.
U.S. Appl. No. 16/950,064, filed Nov. 17, 2020, Limem et al.
U.S. Appl. No. 17/486,886, filed Sep. 27, 2021, Limem et al.
U.S. Appl. No. 29/735,730, filed May 22, 2020, Limem et al.
U.S. Appl. No. 29/736,445, filed May 9, 2020, Limem et al.
U.S. Appl. No. 29/798,823, filed Jul. 10, 2021, Limem et al.
PCT/US2019/015849, Apr. 23, 2019, International Search Report and Written Opinion.
PCT/US2019/015849, Aug. 20, 2020, International Preliminary Report on Patentability.
Extended European Search Report for European Application 19869949.8 dated May 31, 2022.
Extended European Search Report dated Jul. 25, 2023 for European Application No. 23162281.2.

* cited by examiner

FULL CONTOUR BREAST IMPLANT

CROSS-REFERENCE TO RELATED APPLICATIONS

This application is a divisional of U.S. application Ser. No. 16/262,018, filed Jan. 30, 2019, which claims the benefit of U.S. Provisional Application Ser. No. 62/628,739, filed Feb. 9, 2018, both of which are incorporated herein by reference in their entireties.

FIELD OF THE INVENTION

The present invention generally relates to absorbable implants that can be used to shape the volumetric distribution of the breast soft tissue in the upper and lower poles of the breast, the projection of the breast, the curvatures of the upper and lower poles of the breast, and the position and angulation of the nipple, and are designed for use in plastic surgery procedure.

BACKGROUND OF THE INVENTION

Numerous plastic surgery procedures are performed each year to restore or correct the form or function of the body. Many of these procedures seek to restore a youthful appearance, or even to enhance one's existing appearance. Natural factors, such as aging and gravity, contribute to the loss of the youthful appearance. For example, skin laxity, loss of muscle tone, and attenuation of ligaments can result in ptosis (drooping) of the breast. Plastic surgeons have developed a plethora of surgical techniques to correct the ptosis of different anatomical structures that occurs with aging. These techniques vary in the type of incision, direction of incision, plane of dissection, amount of dissection, extent of repositioning of tissue, the use of different types of sutures, different suturing techniques, and different fixation techniques. Almost all of them rely on the use of the pre-existing skin envelope as the support system for the newly lifted tissue. These approaches almost invariably result in recurrent ptosis, since the surgeon is merely relying on the aging and sagging surrounding tissues that have already failed to provide the necessary support to maintain a normal appearance. For example, de-epithelialization, flap transposition, gland repositioning or suturing will not alter the physical properties of the patient's tissue. At most, these techniques only slow recurrent ptosis by creating internal scars that provide limited reinforcement. And even the scarring process varies from patient to patient making this limited approach highly unpredictable. Notably, there is no attempt with these approaches to change the physical properties of the local tissue in order to improve the outcome.

Several surgeons have attempted to reinforce their lift procedures using surgical meshes in mastopexy and breast reconstruction procedures. Some of these techniques have also incorporated the use of various reinforcing materials similar to those used in hernia repair, such as flat polymeric meshes, allografts, xenografts and autografts.

In 1981, Johnson described the use of MARLEX® (crystalline polypropylene) mesh to convert the support of breast tissue after mastopexy from a cutaneous origin to a skeletal origin by attaching the mesh to the area of the second rib, (Johnson, *Aesth. Plast. Surg.* 5:77-84 (1981)). The flat MARLEX® mesh is a permanent mesh made from polypropylene, and was implanted to provide two slings in each breast that supported the breast tissue. It is not replaced with regenerated host tissue.

Auclair and Mitz have described a mesh assisted mastopexy using a flat absorbable mesh and a periareolar skin resection technique (Auclair and Mitz, *Ann. Chir. Plast. Esthdt.* 38:107-113 (1993)). A rapidly absorbing VICRYL® mesh was placed around the anterior surface of the breast gland in order to form an internal bra.

Goes has reported the use of polyglactin 910 (an absorbable copolymer of 90% glycolide and 10% L-lactide, also known as VICRYL®) and a mixed mesh (containing 60% polyglactine 910 and 40% permanent polyester) in a periareolar mammoplasty using a double skin technique (Góes, *Plast. Reconstr. Surg.* 97:959-968 (1996)). The technique involves dissecting the soft tissue envelope away from the parenchyma, and wrapping the breast parenchyma with a mesh to help provoke the formation of a vigorous connective scar to produce a breast lining structure that would be less susceptible to ptosis. The soft tissue envelope is then closed around the parenchyma. In the procedure, a dermal flap was created around the nipple-areolar complex, and after the lift procedure was completed, the dermal flap was sutured on top of the breast gland to provide an internal cutaneous lining. The mesh was then sutured on top of the dermal flap so that it surrounded the breast gland, and the ends of the mesh were sutured together in the central part of the superior aspect of the breast to form a conical breast shape with slight elevation of the breast. Although the mesh was found to provide short-term support, it was absorbed after 3 months, and better results were reported with the mixed (partially absorbable) mesh. The latter provided a less elastic envelope, avoided tissue displacement, and improved the quality and duration of the new breast shape (Sampaio Góes, *Clin. Plast. Surg.* 29:349-64 (2002)).

U.S. Pat. No. 6,210,439 to Firmin et al. discloses a circular VICRYL® mesh with a V-shaped opening extending from its center that has a metallic reinforcing wire running around the periphery. The implant assumes a conical shape suitable for mammoplasty when the reinforcing wire is tightened.

However, VICRYL® mesh degrades rapidly in vivo with 50% loss of strength retention at five days, no residual strength at 10-14 days, and complete absorption at 42 days. This strength retention profile provides very little time for the formation of regenerated host tissue that can withstand the forces exerted on the breast. In fact, Góes and Bates concluded "absorbable synthetic meshes do not persist sufficiently to have an impact on the recurrence of breast ptosis" [see Goes and Bates, Periareolar mastopexy with FortaPerm, *Aesth. Plast. Surg* 34:350-358 (2010)].

U.S. Pat. No. 7,476,249 to Frank discloses an implantable sling shaped prosthesis device for supporting and positioning a breast implant in a patient, wherein the device is configured from a sheet of a chemically inert permanent material, such as polytetrafluoroethylene or silicone, to support the breast implant. The sling shaped device provides support to the breast but does not have shape memory that allows it to confer shape to the breast or retain a three-dimensional shape.

US Patent Application Publication No. 2009/0082864 by Chen et al. also discloses a prosthetic device for supporting a breast implant made from a mesh. The device has a flat back wall, a concave front wall, and a curved transitional region between these walls that forms a smoothly curved bottom periphery.

U.S. Pat. No. 7,670,372 to Shfaram et al. discloses a minimally invasive breast lifting system. The system incorporates a biological material, such as tendons, or synthetic material, such as silicone or GOR-TEX® material (polytetrafluoroethylene), to cradle the breast.

US Patent Application Publication No. 2012/0283826 by Moses et al. discloses mastopexy systems having an insertion device, a suspension strut, and a lower pole support. The implanted suspension strut provides pole projection and attachment points for the lower pole support, and the lower pole support can lift the lower pole of the breast.

US Patent Application Publication No. 2008/0097601 by Codori-Hurff et al. discloses mastopexy and breast reconstruction procedures assisted by the use of processed tissue material derived from intestine or dermis. The tissue material is cut to a crescent shape, and may have up to 10 layers bonded together. The bonded layers can be chemically cross-linked.

US Patent Application Publication No. 2008/0027273 by Gutterman discloses a minimally invasive mastopexy system having a soft tissue support sling. The latter can be made from polyethylene, PEBAX® (polyether block amide), PEEK (polyether ether ketone), nylon, PET (polyethylene terephthalate), ePTFE (polytetrafluoroetylene), silicone, or even a metal lattice. The device is designed to provide support by suspending the breast from the upper pole region using a bone anchor.

US Patent Application Publication No. 2010/0331612 by Lashinski et al. discloses a system for performing a minimally invasive mastopexy (breast lift) that can include an elongate flexible sling used as a soft tissue anchor. The sling can be made from a mesh, and the mesh can be made, for example, from polypropylene. The sling is designed to resist weakening or degradation when implanted.

US Patent Application No. 20100217388 to Cohen discloses cradling members for soft tissue shaping of the breast.

US Patent Application No. 20160038269 to Altman discloses various implants for supporting the breast after surgery. The implants are made from silk.

US Patent Application Publication No. 20120185041 to Mortarino et al. discloses methods for using silk meshes in breast augmentation and breast reconstruction with a knit pattern that substantially prevents unraveling when cut. Mortarino does not disclose silk meshes with three-dimensional shapes that confer shape to the breast.

US Patent Application No. 20130304098 to Mortarino discloses implants in the form of pockets that can be used in breast reconstruction. The implants are made from silk.

Notably, there is very little innovation in the design of implants that when implanted can simplify breast surgery, provide specific shapes to the upper and lower poles of the breast, and angulate the nipple at a desirable projection above the nipple meridian reference (NMR) line.

Mallucci and Branford, Concepts in aesthetic breast dimensions: Analysis of the ideal breast, *JPRAS*, 65:8-16 (2010) analyzed the vertical heights in the coronal plane of the upper and lower poles of the breasts of 100 models, and concluded that the ideal ratio of the vertical height of the upper pole of the breast to the vertical height of the lower pole of the breast in the coronal plane should be 45:55. Any significant deviation from this ratio was considered to result in a less attractive breast shape. The authors subsequently used these findings to develop an improved method for breast augmentation using permanent breast implants (see Mallucci and Branford, Design for natural breast augmentation: The ICE principle, *Plast. Reconstr. Surg.* 137:1728-1737 (2016)). However, amongst other things, the investigators did not describe or show implants to redistribute volume, depth, or slope in the breast to simplify the augmentation procedure and achieve consistent results.

WO 2009/001293 to Lauryssen discloses a permanent implant (made from polypropylene or polyester) in the shape of a cup, more specifically a semi-ovoid shape, that can be used in mesh assisted mastopexy. The described cup has a lower end that is larger than its upper end. The described implant also has a convex lower pole curve and a convex upper pole curve as shown in FIG. 3 of WO 2009/001293 to Lauryssen. The implant is not designed to angulate the patient's nipple. Rather the implant has an aperture for the nipple areola complex that is located more inferior than superior (as shown in FIG. 3 of WO 2009/001293).

WO 2006/117622 by Lauryssen et al. also discloses a permanent implant for soft tissue support of the breast that is generally L-shaped or U-shaped, but is made from polypropylene.

A permanent implant for soft tissue support, made from polytetrafluoroethylene (ePTFE), which can be used in forming a predetermined breast shape has been disclosed by WO 2004/096098 by Hamilton el al. The implants do not degrade in vivo, and are not designed to angulate the patient's nipple above the nipple meridian reference (NMR) line.

Van Deventer et al. has reported the use of an internal breast support system for mastopexy using a partially degradable mesh that was formed into a cone by overlapping the ends of the mesh (van Deventer et al. *Aesth. Plast. Surg.* 36:578-89 (2012)). The mesh contained 50% polypropylene and 50% absorbable polyglactin.

U.S. Pat. No. 9,532,867 to Felix discloses absorbable implants for breast surgery that support newly lifted breast parenchyma. The shapes of the implants include generally symmetrical shapes such as domes, and hemispheres.

Despite the advances described above, surgeons still lack an implant that can produce a defined aesthetically pleasing outcome in breast surgery without extensive manipulation of tissues and use of implants, including sutures, meshes and permanent breast implants.

SUMMARY OF THE INVENTION

Implants described herein assist the surgeon in reshaping the breast with a predefined aesthetically pleasing shape.

In embodiments, an implant is engineered with a desired shape that produces specific volumetric ratios of soft tissue in the upper and lower poles of the breast.

In embodiments, the implant produces a specific angulation of the nipple, specific curvatures of the upper and lower poles, and controls the extent of protrusion of the breast from the chest wall. The surgeon is able to show the implant options to the patient prior to surgery so the patient can select a specific size, and better appreciate the expected outcome of surgery.

In embodiments, in addition to providing a specific breast shape, the implant is absorbable, permits tissue in-growth, degrades in a controlled manner, and is replaced over time with the patient's own tissue. The implant preferably comprises a polymeric material with a predictable rate of degradation, and a predictable strength retention in vivo.

In embodiments, the implant retains strength long enough to allow the support of the breast to be transitioned from the implant to new tissue without any loss of support for the breast tissue.

In embodiments, the implant has a pre-determined three-dimensional shape that can be implanted subcutaneously to cover the entire breast, between the skin and the breast mound of the breast, excluding the nipple areolar complex (NAC). The implant allows the surgeon to easily control the volumetric ratios of the upper and lower poles of the breast, the extent of protrusion of the breast from the chest wall, and the curvatures of the upper and lower poles of the breast.

In embodiments, the implant has a full contour design and provides a means for the surgeon to produce a breast with a highly desirable appearance allowing the shapes and volumes of the upper and lower breast to be re-modeled in a single procedure. In addition, the implant allows the surgeon to position and angle the nipple on the breast at a very desirable, slightly skyward, location.

In embodiments, the implant serves to provide the surgeon with a means to deliver cells, stem cells, gels, hydrogels, bioactive agents, fatty tissue, autologous fat, fat lipoaspirate, injectable fat, adipose cells, fibroblast cells, and other materials to the implant site.

In embodiments, the breast implant is used with a permanent breast implant, such as a silicone or saline breast implant. The implant could also comprise bioactive agents. In other embodiments, the implant is designed to produce a specific breast shape and angulation of the nipple. These implants are configured/designed to produce a breast shape with a specific volumetric ratio of the upper pole volume to the lower pole volume.

In embodiments, implants are configured/designed to produce a specific breast shape where the nipple is angulated at an angle that is 12-27 degrees above the nipple meridian reference (NMR) line, more preferably 18-22 degrees above the NMR.

In embodiments, the implants are porous and absorbable, with an opening for the nipple areola structure, function as transitory scaffolds that contour the breast and provide initial support to the breast, but degrade over time, and are replaced with host tissue. The implants can be used without or with permanent breast implants. The implants are preferably sutured in place, and have suture pullout strengths that are sufficient to resist the mechanical loads exerted on the implant. The implants can be made from poly-4-hydroxybutyrate (P4HB) and copolymers thereof. In embodiments, implants can be made from P4HB and copolymers thereof in the form of a mesh, and preferably a monofilament mesh.

In one embodiment, the implants have a three-dimensional shape that: (i) can redistribute or organize the tissue volume in the breast such that the upper pole volume (UPV) of the breast is between 20-40%, and more preferably 25-35%, and the lower pole volume (LPV) of the breast is between 60-80%, and more preferably 65-75%, and more preferably where the ratio of the UPV to LPV ranges from 20:80 to 40:60, and more preferably from 25:75 to 35:65, and in one embodiment is 28:72, and (ii) angulates the patient's nipple 12 (or 13) to 27 degrees above the nipple meridian reference (NMR) line, more preferably 18-22 degrees above the NMR line. The implants comprise an opening for the nipple areola structure. The implants are preferably absorbable and porous, and replaced in vivo by host tissue.

In embodiments, an implant is configured to redistribute the tissue volume in the breast such that the upper pole volume (UPV) of the breast is between 20-40% and the lower pole volume (LPV) of the breast is between 60-80%, and wherein the implant angulates the patient's nipple 12 (or 13) to 27 degrees above the nipple meridian reference (NMR) line, more preferably 18-22 degrees above the NMR line. The use of a pre-shaped implant for the entire breast that can contour and redistribute tissue volume and angulate the patient's nipple with defined precision would be particularly desirable, and even more desirable if the scaffold is transitory and is replaced over time with host tissue.

In embodiments, an implant is configured to produce a remodeled breast with a UPV of 25-35%, and a LPV of 65-75%, more preferably wherein the ratio of the UPV to the LPV in the breast is 28:72.

In embodiments, an implant is configured to provide a surgeon with an implant for breast surgery that can precisely angulate the patient's nipple, preferably wherein the implant angulates the patient's nipple 12 (or 13) to 27 degrees above the nipple meridian reference (NMR) line, more preferably 18-22 degrees above the NMR line.

In embodiments, an implant is configured to provide a surgeon with an implant for breast surgery that can be used to produce a remodeled breast with a UPV of 25-35%, and a LPV of 65-75%, more preferably wherein the ratio of the UPV to the LPV in the breast is 28:72, and wherein the implant angulates the patient's nipple 12 (or 13) to 27 degrees above the nipple meridian reference (NMR) line, more preferably 18-22 degrees above the NMR line, and wherein the implant is a transitory scaffold that degrades and allows a transition from support of the breast by the scaffold to support by regenerated host tissue.

In an embodiment, an implant is configured with an upper pole, a lower pole, and wherein the ratio of the volume of the upper pole to the lower pole is less than 1.

In an embodiment, an implant is configured with an upper pole, a lower pole, and an aperture for the nipple areola complex (NAC), wherein the ratio of the volume of the upper pole to the lower pole is less than 1, and wherein the aperture is positioned on the implant to angulate the NAC, after implantation, so that the angle between the nipple projection line and the nipple meridian reference line is greater than 1 degree.

In embodiments, a superior end of the implant has a size equal to or greater than the inferior end of the implant.

In embodiments, the implant comprises an annular shaped flexible pillar circumferentially disposed about the NAC aperture.

In embodiments, the implant further comprises a plurality of reinforcing pillars or ribs radially extending from the NAC aperture feature to the outer edge of the implant.

In embodiments, the implant comprises a plurality of tissue-attachment tabs radially extending from a rearward edge the implant. In embodiments, the tabs extend from 3, 6, 9 and 12 o'clock positions.

In embodiments, an implant is configured to provide implants for breast surgery that can be used with or without implants, and that can be temporarily deformed for implantation.

In embodiments, an implant is configured to provide methods to produce implants that can be used to remodel a breast so that the breast has a UPV of 25-35%, and a LPV of 65-75%, more preferably wherein the ratio of the UPV to the LPV in the breast is 28:72, and wherein the implant angulates the patient's nipple 12 (or 13) to 27 degrees above the nipple meridian reference (NMR) line, more preferably 18-22 degrees above the NMR line.

In embodiments, an implant is configured to provide methods to implant the implants, and produce a breast with a UPV of 25-35%, and a LPV of 65-75%, more preferably wherein the ratio of the UPV to the LPV in the breast is 28:72, and wherein the implant angulates the patient's nipple 12 (or 13)-27 degrees above the nipple meridian reference (NMR) line, more preferably 18-22 degrees above the NMR line.

In embodiments, a kit for assisting the physician to reshape the breast comprises a plurality of sterile guides each of which defines a breast shape having an UPV of 25-35% of the total breast volume, and an opening to angulate the patient's nipple between 10-30 degrees.

In embodiments, a method of reshaping the breast of a patient comprises determining at least one target percent that the upper pole of the breast shall occupy relative to the total target volume of the breast; selecting an implant from a kit of candidate implants shaped to hold the mound of the breast such that the upper pole of the breast occupies the target percent of the total breast volume after implantation; and implanting the selected implant into the breast between the breast mound and the skin.

In embodiments, the each of the candidate implants of the kit has a target percent between 25 and 35%.

In embodiments, each of the candidate implants of the kit has a NAC aperture that angulates the nipple between 10-30 degrees skyward.

In embodiments, the lower pole of each of the candidate implants of the kit has a convex curvature.

In embodiments, the upper pole of each of the candidate implants of the kit has a concave curvature, or in other embodiments, is noncurved or straight.

These advantages as well as other objects and advantages of the present invention will become apparent from the detailed description to follow, together with the accompanying drawings.

DETAILED DESCRIPTION OF THE INVENTION

Before the present invention is described in detail, it is to be understood that this invention is not limited to particular variations set forth herein as various changes or modifications may be made to the invention described and equivalents may be substituted without departing from the spirit and scope of the invention. As will be apparent to those of skill in the art upon reading this disclosure, each of the individual embodiments described and illustrated herein has discrete components and features which may be readily separated from or combined with the features of any of the other several embodiments without departing from the scope or spirit of the present invention. In addition, many modifications may be made to adapt a particular situation, material, composition of matter, process, process act(s) or step(s) to the objective(s), spirit or scope of the present invention. All such modifications are intended to be within the scope of the claims made herein.

Methods recited herein may be carried out in any order of the recited events which is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail).

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Figure 1:
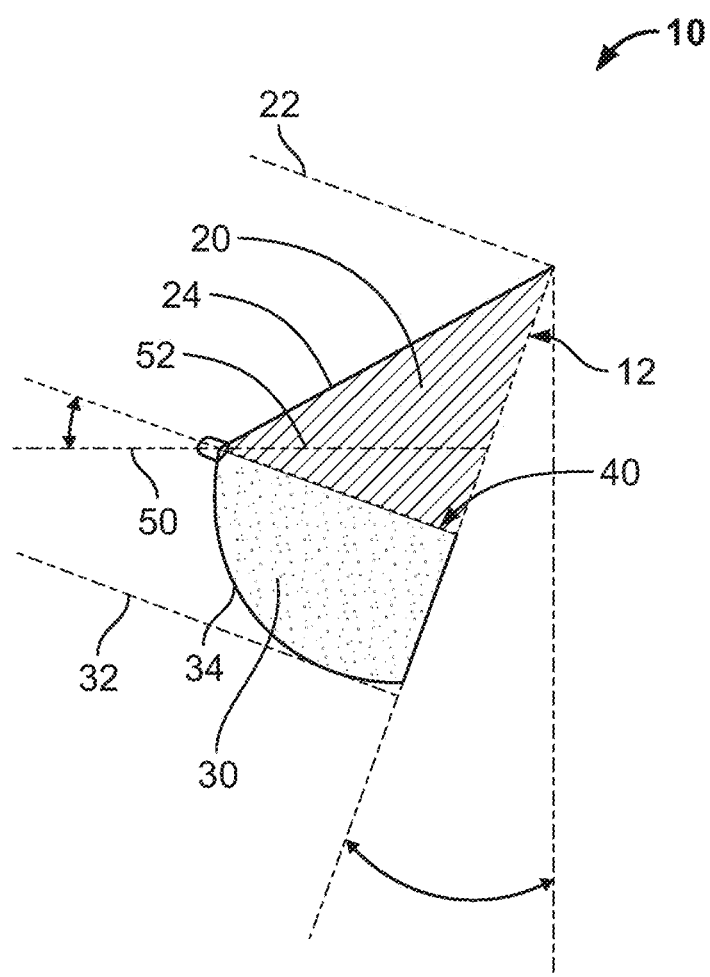
FIGS. 1-5 are side views of a breast shown in various shapes.
Figure 2:
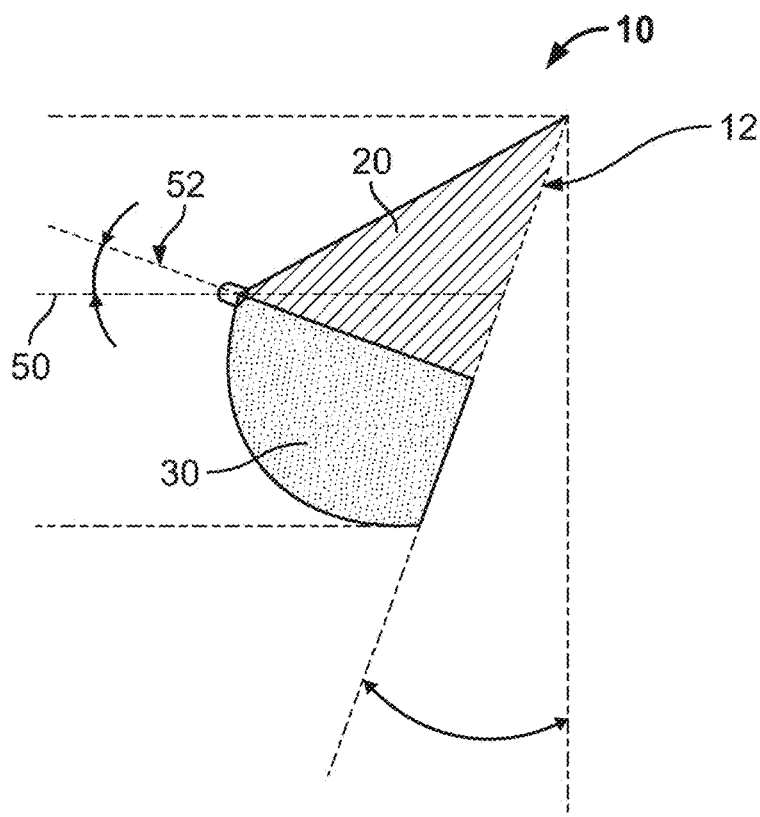

Now turning to FIGS. 1-2, various patient anatomy and anatomical landmarks are depicted for facilitating understanding of the invention. Particularly, FIG. 1 is a diagram showing a cross-section of a breast 10 in an aesthetically pleasing breast shape. The volume or area occupied by the upper pole is shown as the area with the diagonal parallel lines and reference numeral 20. The volume or area occupied by the lower pole is shown as the shaded area and reference numeral 30. The diagram also shows the chest wall reference (CWR) line 12, and positions of the upper pole reference (UPR) 22, upper pole curve (UPC) 24, lower pole reference (LPR) line 32, lower pole curve (LPC) 34, NAC (nipple areolar complex) plane 40, and the angulation of the NAC measured from the nipple meridian reference (NMR) line 50 to the nipple projection line (NPL) 52.

FIG. 2 is another diagram showing a three-quarter profile of the breast, the upper pole volume (UPV) 20 and lower pole volume (LPV) 30 of the breast, the NAC angulation of the nipple on the breast pointing slightly skyward, and a ratio of the height of the upper pole of the breast to the lower pole of the breast equal to 70:40 when measured along the natural sloping chest wall reference (CWR) line 12.

To further assist in understanding the following definitions are set forth below. However, it is also to be appreciated that unless defined otherwise as described herein, all technical and scientific terms used herein have the same meaning as commonly understood by one of ordinary skill in the art to which this invention belongs.

Definitions

"Absorbable" as generally used herein means the material is degraded in the body, and the degradation products are eliminated or excreted from the body. The terms "absorbable", "resorbable", "degradable", and "erodible", with or without the prefix "bio", can be used interchangeably herein, to describe materials broken down and gradually absorbed, excreted, or eliminated by the body, whether degradation is due mainly to hydrolysis or mediated by metabolic processes.

"Bioactive agent" as generally used herein refers to therapeutic, prophylactic or diagnostic agents, preferably agents that promote healing and the regeneration of host tissue, and also therapeutic agents that prevent, inhibit or eliminate infection. "Bioactive agent" includes a single such agent and is also intended to include a plurality.

"Blend" as generally used herein means a physical combination of different polymers, as opposed to a copolymer formed of two or more different monomers.

"Burst strength" as generally used herein is determined according to ASTM D6797-02 (Standard Test Method for Bursting Strength of Fabrics Constant-Rate-of-Extension (CRE) Ball Burst Test) at ambient conditions using a ball burst fixture with a 1.6 cm circular opening and a 1 cm diameter half-rounded probe.

"Copolymers of poly-4-hydroxybutyrate" as generally used herein means any polymer containing 4-hydroxybutyrate with one or more different hydroxy acid units.

"Endotoxin content" as generally used herein refers to the amount of endotoxin present in an implant or sample, and is determined by the limulus amebocyte lysate (LAL) assay.

"Inframammary fold" or "IMF" as generally used herein is the position where the lower pole of the breast meets the chest wall.

"Lower pole" as generally used herein means the part of the breast located between the inframammary fold (IMF) and the nipple meridian reference, and protruding away from the chest wall.

"Lower pole reference" or "LPR" as generally used herein is a line that extends perpendicular from the chest wall, starting just below the inframammary fold, and just touches the lowest projection of the lower pole of the breast as shown in FIG. 1.

"Lower pole volume" or "LPV" as generally used herein means the volume of tissue in the lower pole of the breast as shown in FIG. 2. The volume of tissue is contained within the boundaries defined by the lower pole curve, the chest wall and the nipple projection line (NPL).

"Molecular weight" as generally used herein, unless otherwise specified, refers to the weight average molecular weight (Mw), not the number average molecular weight (Mn), and is measured by GPC relative to polystyrene.

"NAC angulation" or nipple angle as generally used herein means the angle between the nipple meridian reference (NMR) line and the nipple projection line" or "NPL" as shown in FIG. 1.

"Nipple meridian reference" or "NMR" is the plane drawn horizontally through the nipple to the chest wall as shown in FIG. 1.

"Nipple projection line" or "NPL" as generally used herein means the line drawn perpendicular to the chest wall through the nipple as shown in FIG. 1.

"Poly-4-hydroxybutyrate" as generally used herein means a homopolymer containing 4-hydroxybutyrate units. It can be referred to herein as P4HB or TephaFLEX® biomaterial (manufactured by Tepha, Inc., Lexington, MA).

"Suture pullout strength" as generally used herein means the peak load (kg) at which an implant fails to retain a suture. It is determined using a tensile testing machine by securing an implant in a horizontal holding plate, threading a suture in a loop through the implant at a distance of 1 cm from the edge of the implant, and securing the suture arms in a fiber grip positioned above the implant. Testing is performed at a crosshead rate of 100 mm/min, and the peak load (kg) is recorded. The suture is selected so that the implant will fail before the suture fails.

"Upper pole" as generally used herein means the top part of the breast located between the upper pole reference and the nipple meridian reference, and protruding away from the chest wall.

"Upper pole reference" or "UPR" as generally used herein is the position at the top of the breast where the breast takes off from the chest wall, and is shown in FIG. 1.

"Upper pole volume" or "UPV" as generally used herein means the volume of tissue in the upper pole of the breast as shown in FIG. 2. The volume of tissue is contained within the boundaries defined by the upper pole curve, the chest wall and the nipple projection line (NPL).

Materials for Preparing Full Contour Breast Implants

In embodiments, implants that can be used to remodel the shape of the breast, the upper and lower pole volumes, the protrusion of the breast from the chest wall, and the angulation of the nipple on the breast have been developed using a wide variety of materials. The implants produce safe biocompatible and an aesthetically pleasing breast by redistributing and organizing tissue volume in the breast so that there is a specific volumetric ratio of tissue in the upper breast relative to the lower breast, specific curvatures of the upper pole and lower pole, and specific angulation of the nipple on the breast. Optionally, the implants may be used with permanent breast implants such as silicone and saline breast implants as well as other bulking materials and tissues.

A. Polymers for Preparing Full Contour Breast Implants

The full contour breast implants may comprise permanent materials, such as non-degradable thermoplastic polymers, including polymers and copolymers of ethylene and propylene, including ultra-high molecular weight polyethylene, ultra-high molecular weight polypropylene, nylon, polyesters such as poly(ethylene terephthalate), poly(tetrafluoroethylene), polyurethanes, poly(ether-urethanes), poly(methylmethacrylate), polyether ether ketone, polyolefins, and poly(ethylene oxide). However, the implants preferably comprise degradable materials, more preferably thermoplastic or polymeric degradable materials, and even more preferably the implants are made completely from degradable materials.

In a preferred embodiment, the implants are made from one or more absorbable polymers, preferably absorbable thermoplastic polymers and copolymers. The implant may, for example, be prepared from polymers including, but not limited to, polymers of glycolic acid, lactic acid, 1,4-dioxanone, trimethylene carbonate, 3-hydroxybutyric acid, 4-hydroxybutyrate, ε-caprolactone, including polyglycolic acid, polylactic acid, polydioxanone, polycaprolactone, copolymers of glycolic and lactic acids, such as VICRYL® polymer, MAXON® and MONOCRYL® polymers, and including poly(lactide-co-caprolactones); poly(orthoesters); polyanhydrides; poly(phosphazenes); polyhydroxyalkanoates; synthetically or biologically prepared polyesters; polycarbonates; tyrosine polycarbonates; polyamides (including synthetic and natural polyamides, polypeptides, and poly (amino acids)); polyesteramides; poly(alkylene alkylates); polyethers (such as polyethylene glycol, PEG, and polyethylene oxide, PEO); polyvinyl pyrrolidones or PVP; polyurethanes; polyetheresters; polyacetals; polycyanoacrylates; poly(oxyethylene)/poly(oxypropylene) copolymers; polyacetals, polyketals; polyphosphates; (phosphorous-containing) polymers; polyphosphoesters; polyalkylene oxalates; polyalkylene succinates; poly(maleic acids); silk (including recombinant silks and silk derivatives and analogs); chitin; chitosan; modified chitosan; biocompatible polysaccharides; hydrophilic or water soluble polymers, such as polyethylene glycol, (PEG) or polyvinyl pyrrolidone (PVP), with blocks of other biocompatible or biodegradable polymers, for example, poly(lactide), poly(lactide-co-glycolide, or polycaprolactone and copolymers thereof, including random copolymers and block copolymers thereof. Preferably the absorbable polymer or copolymer will be substantially resorbed after implantation within a 1 to 24-month timeframe, more preferably 3 to 18-month timeframe, and retain some residual strength for at least 2 weeks to 3 months.

Blends of polymers, preferably absorbable polymers, can also be used to prepare the full contour breast implants. Particularly preferred blends of absorbable polymers are prepared from absorbable polymers including, but not limited to, polymers of glycolic acid, lactic acid, 1,4-dioxanone, trimethylene carbonate, 3-hydroxybutyric acid, 4-hydroxybutyrate, ε-caprolactone or copolymers thereof.

In a particularly preferred embodiment, poly-4-hydroxybutyrate (Tepha's P4HB™ polymer, Lexington, MA) or a copolymer thereof is used to make the implant. Copolymers include P4HB with another hydroxyacid, such as 3-hydroxybutyrate, and P4HB with glycolic acid or lactic acid monomer. Poly-4-hydroxybutyrate is a strong, pliable thermoplastic polyester that is biocompatible and resorbable (Williams, et al. Poly-4-hydroxybutyrate (P4HB): a new generation of resorbable medical devices for tissue repair and regeneration, *Biomed. Tech.* 58(5):439-452 (2013)). Upon implantation, P4HB hydrolyzes to its monomer, and the monomer is metabolized via the Krebs cycle to carbon dioxide and water. In a preferred embodiment, the P4HB homopolymer and copolymers thereof have a weight average molecular weight, Mw, within the range of 50 kDa to 1,200 kDa (by GPC relative to polystyrene) and more preferably from 100 kDa to 600 kDa. A weight average molecular weight of the polymer of 50 kDa or higher is preferred for processing and mechanical properties.

B. Additives

Certain additives may be incorporated into the implant, preferably in the absorbable polymer, copolymer or blends thereof that are used to make the implant. Preferably, these additives are incorporated during a compounding process to produce pellets that can be subsequently melt-processed. For example, pellets may be extruded into fibers suitable for making the implants. In another embodiment, the additives may be incorporated using a solution-based process, for example, fibers may be spun from solutions of the polymer and one or more additives. In a preferred embodiment, the additives are biocompatible, and even more preferably the additives are both biocompatible and resorbable.

In one embodiment, the additives may be nucleating agents and/or plasticizers. These additives may be added in sufficient quantity to produce the desired result. In general, these additives may be added in amounts between 1% and 20% by weight. Nucleating agents may be incorporated to increase the rate of crystallization of the polymer, copolymer or blend. Such agents may be used, for example, to facilitate fabrication of the implant, and to improve the mechanical properties of the implant. Preferred nucleating agents include, but are not limited to, salts of organic acids such as calcium citrate, polymers or oligomers of PHA polymers and copolymers, high melting polymers such as PGA, talc, micronized mica, calcium carbonate, ammonium chloride, and aromatic amino acids such as tyrosine and phenylalanine.

Plasticizers that may be incorporated into the compositions for preparing the implants include, but are not limited to, di-n-butyl maleate, methyl laureate, dibutyl fumarate, di(2-ethylhexyl) (dioctyl) maleate, paraffin, dodecanol, olive oil, soybean oil, polytetramethylene glycols, methyl oleate, n-propyl oleate, tetrahydrofurfuryl oleate, epoxidized linseed oil, 2-ethyl hexyl epoxytallate, glycerol triacetate, methyl linoleate, dibutyl fumarate, methyl acetyl ricinoleate, acetyl tri(n-butyl) citrate, acetyl triethyl citrate, tri(n-butyl) citrate, triethyl citrate, bis(2-hydroxyethyl) dimerate, butyl ricinoleate, glyceryl tri-(acetyl ricinoleate), methyl ricinoleate, n-butyl acetyl rincinoleate, propylene glycol ricinoleate, diethyl succinate, diisobutyl adipate, dimethyl azelate, di(n-hexyl) azelate, tri-butyl phosphate, and mixtures thereof. Particularly preferred plasticizers are citrate esters.

C. Bioactive Agents

The implants can be loaded or coated with bioactive agents. Bioactive agents may be included in the implants for a variety of reasons. For example, bioactive agents may be included in order to improve tissue in-growth into the implant, to improve tissue maturation, to provide for the delivery of an active agent, to improve wettability of the implant, to prevent infection, and to improve cell attachment. The bioactive agents may also be incorporated into the structure of the implant.

The implants may contain cellular adhesion factors, including cell adhesion polypeptides. As used herein, the term "cell adhesion polypeptides" refers to compounds having at least two amino acids per molecule that are capable of binding cells via cell surface molecules. The cell adhesion polypeptides include any of the proteins of the extracellular matrix which are known to play a role in cell adhesion, including fibronectin, vitronectin, laminin, elastin, fibrinogen, collagen types I, II, and V, as well as synthetic peptides with similar cell adhesion properties. The cell adhesion polypeptides also include peptides derived from any of the aforementioned proteins, including fragments or sequences containing the binding domains.

The implants can incorporate wetting agents designed to improve the wettability of the surfaces of the implant structures to allow fluids to be easily adsorbed onto the implant surfaces, and to promote cell attachment and or modify the water contact angle of the implant surface. Examples of wetting agents include polymers of ethylene oxide and propylene oxide, such as polyethylene oxide, polypropylene oxide, or copolymers of these, such as PLURONICS®. Other suitable wetting agents include surfactants or emulsifiers.

The implants can contain gels, hydrogels or living hydrogel hybrids to further improve wetting properties and to promote cellular growth throughout the thickness of the scaffold. Hydrogel hybrids consist of living cells encapsulated in a biocompatible hydrogel like gelatin, methacrylated gelatin (GelMa), silk gels, and hyaluronic acid (HA) gels.

The implants can contain active agents designed to stimulate cell in-growth, including growth factors, cellular differentiating factors, cellular recruiting factors, cell receptors, cell-binding factors, cell signaling molecules, such as cytokines, and molecules to promote cell migration, cell division, cell proliferation and extracellular matrix deposition. Such active agents include fibroblast growth factor (FGF), transforming growth factor (TGF), platelet derived growth factor (PDGF), epidermal growth factor (EGF), granulocyte-macrophage colony stimulation factor (GMCSF), vascular endothelial growth factor (VEGF), insulin-like growth factor (IGF), hepatocyte growth factor (HGF), interleukin-1-B (IL-1 B), interleukin-8 (IL-8), and nerve growth factor (NGF), and combinations thereof.

Other bioactive agents that can be incorporated in the implants include antimicrobial agents, in particular antibiotics, disinfectants, oncological agents, anti-scarring agents, anti-inflammatory agents, anesthetics, small molecule drugs, anti-angiogenic factors and pro-angiogenic factors, immunomodulatory agents, and blood clotting agents. The bioactive agents may be proteins such as collagen and antibodies, peptides, polysaccharides such as chitosan, alginate, hyaluronic acid and derivatives thereof, nucleic acid molecules, small molecular weight compounds such as steroids, inorganic materials such as hydroxyapatite, or complex mixtures such as platelet rich plasma. Suitable antimicrobial agents include: bacitracin, biguanide, triclhosan, gentamicin, minocycline, rifampin, vancomycin, cephalosporins, copper, zinc, silver, and gold. Nucleic acid molecules may include DNA, RNA, siRNA, miRNA, antisense or aptamers.

The implants may also contain allograft material and xenograft materials, including acellular dermal matrix material and small intestinal submucosa (SIS).

Additionally, human fat such as autologous fat grafts may be added or injected across or into the implant scaffolding. Lipoaspirate fatty tissue from the patient may be added to the internal surface or external surface of the implant. In the case that the implant is porous, the fatty tissue and globules may be held in place within the pores of the implant.

In another embodiment, the collected fatty tissue is mixed with a natural or synthetic fluidized scaffolding matrix to be added to the implant to assist in holding the globules of fat in place in the implant. Examples of natural and synthetic fluidized scaffolding matrix include, without limitation, hydrogels, water soluble polymers, polyesters, and hydrophilic polymers, including polyethylene oxide, polyvinyl alcohol, and polymers of fibrin, thrombin, alginate, collagen, chitosan, and silk.

In yet another preferred embodiment, the implants may incorporate systems for the controlled release of the therapeutic or prophylactic agents.

Components for Preparing Full Contour Breast Implants

A variety of methods can be used to manufacture the implants. The implants may comprise the fibers disclosed herein.

Fibers for Making Full Contour Implants

The implants may comprise fibers. The fibers are made from degradable thermoplastic polymers, and even more preferably from degradable thermoplastic polyesters. The fibers are preferably made from the degradable materials listed above. The fibers maybe monofilament fibers, multifilament fibers, or combinations thereof. Particularly preferred implants comprise monofilament fibers. The fibers may be unoriented, partially oriented, highly oriented or combinations thereof, but are preferably oriented. The fibers preferably have elongation to break values of 3% to 100%, more preferably 3% to 50%. The fibers may have diameters ranging from 1 micron to 5 mm, more preferably from 10 microns to 1 mm, and even more preferably from 50 microns to 500 microns. The fibers may have weight average molecular weights ranging from 10 kDa to 1,200 kDa, but more preferably from 50 kDa to 600 kDa. The fibers preferably retain at least 50% of their initial strength in vivo for 1-6 months, more preferably 2-4 months. The fibers preferably completely degrade within 5 years of implantation, and more preferably within 2 years of implantation. The fibers preferably have initial tensile strengths ranging from 1 to 1,300 MPa, and more preferably from 50 MPa to 1,000 MPa.

In an embodiment, the implants comprise fibers with one or more of the following properties: an elongation to break of 10-100%, and a tensile strength of 300-1,000 MPa.

In one preferred embodiment, the full contour implants comprise fibers made from P4HB, and more preferably from P4HB monofilament fiber. The P4HB monofilament fibers are preferably partially or fully oriented (i.e. partially or fully stretched after extrusion). In one embodiment, P4HB monofilament fiber may be produced according to the following method. Bulk P4HB resin in pellet form is dried to under 300 ppm water using a rotary vane vacuum pump system. The dried resin is transferred to an extruder feed hopper with nitrogen purge to keep the pellets dry. The pellets are gravity fed into a chilled feeder section and introduced into an extruder barrel, with a 1.5 inch (3.8 cm) diameter, and fitted with an extrusion screw with a 30:1 L/D ratio. The extruder barrel preferably contains 5 heating zones (or extrusion zones), and is manufactured by American Kuhne. The heated and softened resin from the extruder is fed into a heated metering pump (melt pump) and from the melt pump the extruded resin is fed into the heated block and an 8-hole spinneret assembly. Processing profile ranges from 40° C. to 260° C. for temperatures, and 400 psi to 2000 psi for pressures. The molten filaments are preferably water quenched and optionally conveyed into an orientation line, preferably a three-stage orientation line, and optionally with inline relaxation, before winding of the monofilaments on spools. This procedure may, for example, be used to produce P4HB monofilament fibers with one or more of the following properties: an elongation to break from 10-100%, a tensile strength from 50-1,300 MPa, and a tensile modulus from 70-1,000 MPa. The P4HB monofilament fibers may have average diameters ranging from 20 microns to 1 mm, but are more preferably 50 microns to 500 microns. In an embodiment, the P4HB monofilament fibers may have USP (United States Pharmacopeia) sizes 10, 9, 8, 7, 6, 5, 4, 3, 2, 1, 0, 2-0, 3-0, 4-0, 5-0, 6-0, 7-0, 8-0, 9-0, 10-0, 11-0, and 12-0.

In another embodiment, the full contour implants comprise fibers made from P4HB multifilament fiber. Multifilament fibers of P4HB or copolymers thereof may be spun, for example, as follows: The polymer, copolymer or blend thereof is pelletized, and dried so that the moisture content of the polymer, copolymer or blend is less than 300 ppm. The dried pellets are placed in the feed hopper of an extruder, and protected from moisture, for example with a dry nitrogen purge. The pellets are gravity fed into a chilled feeder section, and introduced into a suitable extruder barrel with an extrusion screw. One suitable extruder barrel has a diameter of 0.75 inches and length of 25.69 inches, and is fitted with an extrusion screw with a 30:1 L/D ratio. American Kuhne makes a suitable extruder. In a preferred embodiment, the extruder barrel contains 4 heating zones, and a processing profile is set with temperatures ranging from 40° C. to 300° C. and pressures of 200 psi to 3,000 psi. The heated and softened polymer, copolymer or blend is fed into a metering pump, and from the metering pump the resin is fed into the heated block. The spin head is fitted with a spin pack comprising filtering media (screens), and spinnerets containing the desired number of holes for forming the individual filaments of the multifilament yarn. For example, the spinneret may have 15, 30, 60, 120 or more or less holes. The extruded filaments exit the spinneret, and pass through a heated chimney before they are allowed to cool. Spin finish is preferably applied to the yarn, and the yarn may either be collected on a winder, or oriented in-line. Suitable spin finishes include PEG400 and Tween 20. The multifilament fiber may have a tenacity between 1 and 12 grams per denier.

P4HB Meshes

The fibers described herein may be processed into meshes, for example, by knitting, weaving, or crocheting. A particularly preferred mesh for use in preparing the full contour implants is a warp knit mesh.

Implants comprising knitted meshes may be produced using P4HB fibers, preferably P4HB monofilament fibers. Implants comprising P4HB monofilament oriented or partially oriented fibers have a prolonged strength retention profile, and can maintain some residual strength for as much as one year. The prolonged strength retention of these P4HB fibers provides an extended period for tissue in-growth into the meshes made from these fibers, and therefore full contour breast implants made from P4HB meshes can prevent early recurrent ptosis while regenerated tissue is formed around and in the mesh scaffold to support the breast.

A suitable knitted P4HB mesh may be prepared, for example, by the following method. Monofilament fibers from 49 spools are pulled under uniform tension to the surface of a warp beam. A warp is a large wide spool onto which individual fibers are wound in parallel to provide a sheet of fibers ready for coating with a 10% solution of Tween® 20 lubricant. Tween® 20 lubricant is added to the surface of the sheet of fiber by means of a 'kiss' roller that is spinning and is immersed in a bath filled with Tween® 20. The upper surface of the roller is brought into contact with the sheet of fiber, and the roller spun at a uniform speed to provide a consistent application of Tween® 20 finish. Following the application of Tween® 20, the sheet of fiber is placed onto a creel position such that each spooled fiber is aligned and wrapped side by side to the next spooled fiber on a warp beam. Next, warp beams are converted into a finished mesh fabric by means of interlocking knit loops. Eight warp beams are mounted in parallel onto a tricot machine let-offs and fed into the knitting elements at a constant rate determined by the 'runner length'. Each individual monofilament fiber from each beam is fed through a series of dynamic tension elements down into the knitting 'guides'. Each fiber is passed through a single guide, which is fixed to a guide bar. The guide bar directs the fibers around the needles forming the mesh structure. The mesh fabric is then pulled off the needles by the take down rollers at a constant rate of speed. The mesh fabric is then taken up and wound onto a roll. The P4HB monofilament mesh produced according to this method may be scored ultrasonically with water, optionally heat set in hot water, and optionally washed with a 70% aqueous ethanol solution.

Methods for Preparing Full Contour Breast Implants

A variety of methods can be used to manufacture the full contour implants.

Shapes

In an embodiment, the absorbable implants are designed so that when manufactured, they are three-dimensional. Their shape allows the breast to be contoured, and the volumes of the upper and lower pole to be controlled without any buckling or bunching of the implant or tissue structures. The implants have volumetric dimensions that produce specific breast shapes when implanted. Specifically, the implant's volumetric dimensions sculpt the breast so that the ratio of the upper pole volume (UPV) to the lower pole volume (LPV) is pre-defined by the implant. Thus, the volumetric dimensions of the implant produce a particular breast appearance wherein the ratio of the UPV to the LPV falls within a relatively narrow range.

Figure 3:
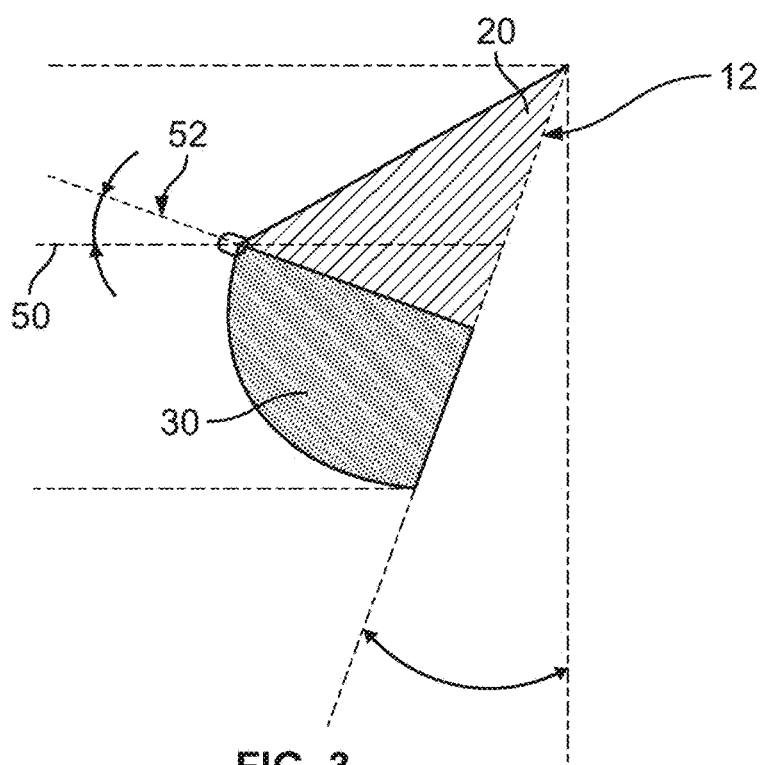

For example, with reference to FIG. 3, an aesthetically pleasing breast 10 is shown having a three-quarter profile, where 28% of the volume of the breast is in the upper pole 20 of the breast, 72% of the volume of the breast is in the lower pole 30 of the breast, the NPL 52 corresponding to the NAC on the breast is angulated slightly skyward, and the ratio of the height of the upper pole of the breast to the lower pole of the breast measured along the natural sloping angle of the chest wall reference (CWR) line 12 is 70:40.

However, the invention is not so limited. In other embodiments, the implants have a three-dimensional shape that results in a breast having one or more of the following properties: (i) an upper pole volume (UPV) of 25-35% of the total breast volume, (ii) lower pole volume (LPV) of 65-75% of the total breast volume, and a nipple angled on the breast pointing slightly skyward at 12-27 degrees above the nipple meridian reference (NMR) line, more preferably 18-22 degrees above the NMR line.

Figure 4A:
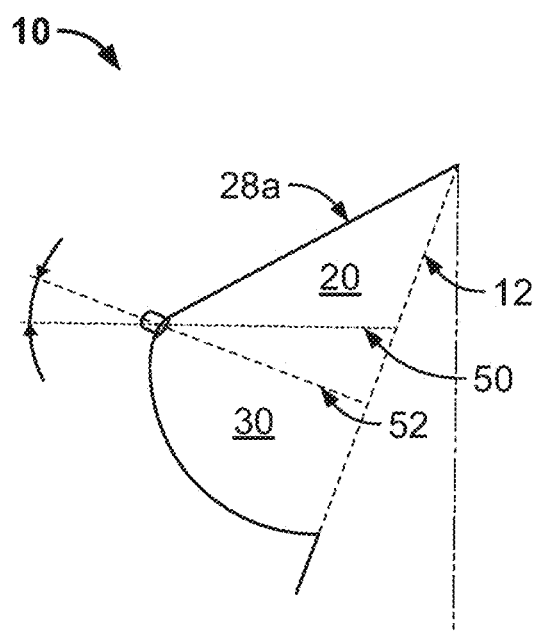
Figure 4B:
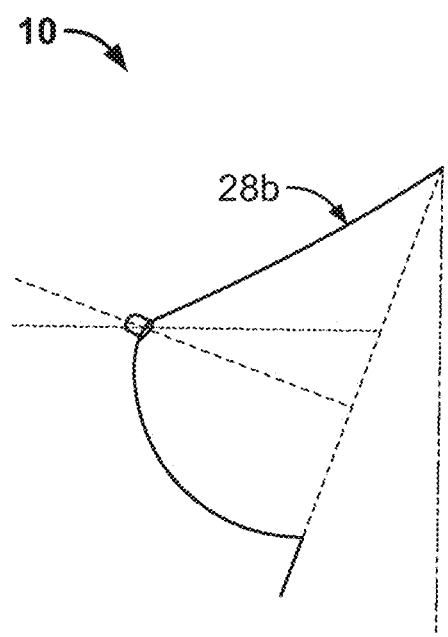

In addition to sculpting the breast with specific volumetric ratios of tissue in the upper and lower poles, the dimensions and shape of the implant can also be chosen to provide very desirable shapes of the lower pole, upper pole, and extent of projection of the breast from the chest wall. In particular, the implants are designed so that (a) the lower pole has a very attractive lower pole curvature, specifically an attractive convex shape, (b) the upper pole has a straight (as shown in FIG. 4A) or slightly concave curvature (as shown in FIG. 4B), and (c) the distance the breast projects from the breast wall is defined.

In a further preferred embodiment, the implant's shape is designed so that the angulation of the patient's nipple can be controlled, and can be placed at a specific position on the reconstructed breast.

Figure 5:
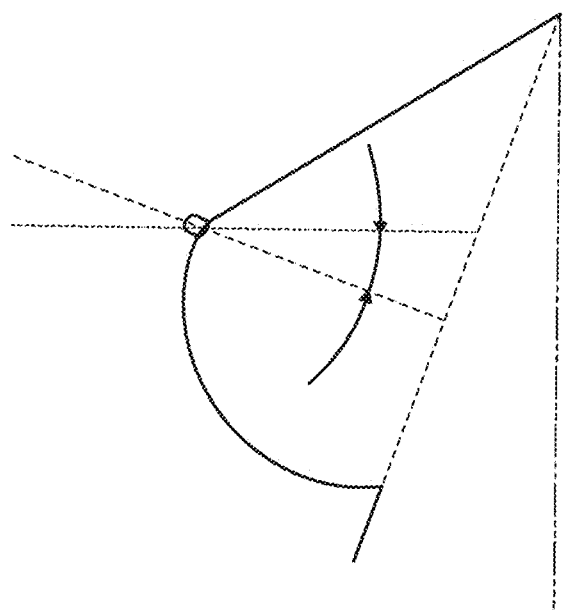

With reference to FIG. 5, the implant is configured to control the position of the patent's nipple so that it is angulated slightly skyward, preferably the nipple is positioned at an angle of 10-30 degrees above the nipple meridian reference (NMR) line, and in some embodiments 12-27 or 13-27 degrees above the NMR line, and more preferably 18-22 degrees above the NMR line. In embodiments, the implant supports or remodels the breast where the nipple is positioned at an angle greater than 10 and less than 20 degrees above the NMR line.

With reference to FIGS. 6A-6D, front, lateral, top and isometric views of a full contour implant 100 are shown respectively. The implant 100 includes a NAC feature 110, guiding flexible pillars 120, and attachment tabs 130 on the outer edge of the implant.

In embodiments, the implants have an opening 110, preferably a circular opening or "NAC feature", through which the nipple areola structure can be placed. The opening 110 can be smooth and may also be reinforced 112 as described further herein.

The implant 100 shows pillars 120 which, as described further herein, reinforce the shape of the implant, and direct the tissue to the predetermined shapes. The pillars may be additional fused material including, e.g., mesh, foam or other material as described herein.

Tabs 130 are shown at the 12-, 3-, 6-, and 9-O-clock positions. As described further herein, tabs 130 provide additional material for the physician to suture or attached the implant in place.

Figure 6D:
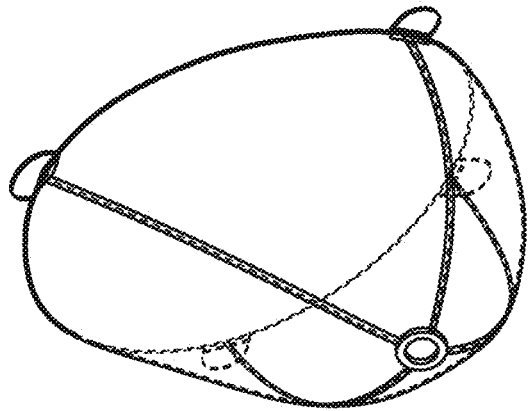
FIGS. 6A-6D show various views of an implant for supporting a breast in accordance with an embodiment of the invention.
Figure 6C:
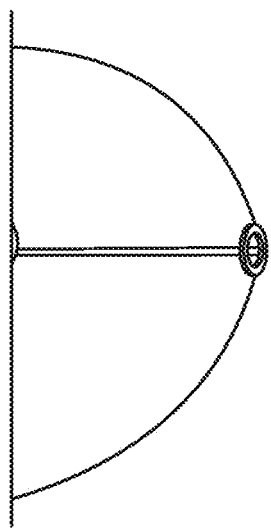
Figure 6A:
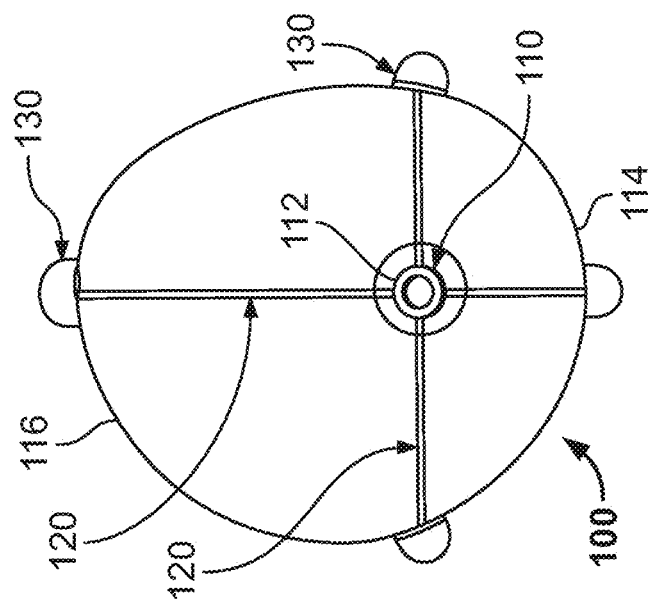
Figure 6B:
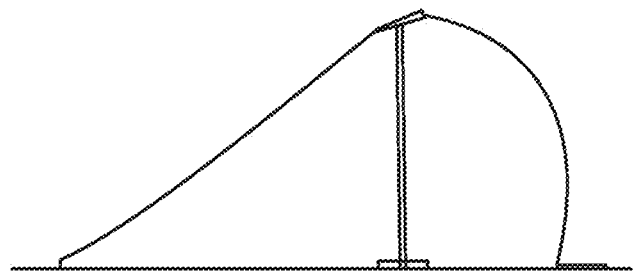

The implant 100 is also shown having a superior end 116 at least as large as the inferior end 114. With reference to FIG. 6B, the UP curvature is straight or a bit concave and the LP curvature is clearly convex It will therefore be apparent that the implants of the invention can be used to produce a very attractive reconstructed breast by having specific shapes that (i) define the ratio of the UPV to the LPV; (ii) define the curvatures of the upper and lower poles; (iii) define the extent of projection of the breast from the chest wall; and (iv) define the angulation of the nipple on the breast.

In order to produce a very attractive reconstructed breast with the specific shapes described herein, the dimensions of the implant are designed to allow for the volume occupied by the skin flap that covers the implant after implantation in the breast. In other words, a breast with a UPV of 25-35% of the total breast volume, and a LPV of 65-75%, is formed as a result of the volume of the implant plus the volume of the skin flap. Typically, a skin flap used by a surgeon to cover the implant will be 0.5-4 cm thick, more preferably 1-3 cm thick, and is generally wider closer to the chest wall than to the NAC. Accordingly, the dimensions of the implant used in the procedure of the invention are not the same as the dimensions of the final reconstructed breast. The implants disclosed herein preferably have an upper pole volume of 20-400%, more preferably 23-35%, and even more preferably 25-31%, and a lower pole volume of 60-80%, more preferably 65-75%, and even more preferably 69-75%. When overlaid with the patient's skin flap, a breast with a UPV of 25-35% and LPV of 65-75% is produced.

In embodiments, the thickness of the implant varies. In embodiments, the thickness from the perimeter to the center or NAC opening decreases. In other embodiments, the thickness from the perimeter to the center or NAC opening increases. As described further herein, the thickness of the implant may be adjusted by adding a layer such as foam, collagen, or fusing additional material to select locations or making redundant layers.

Figure 14:
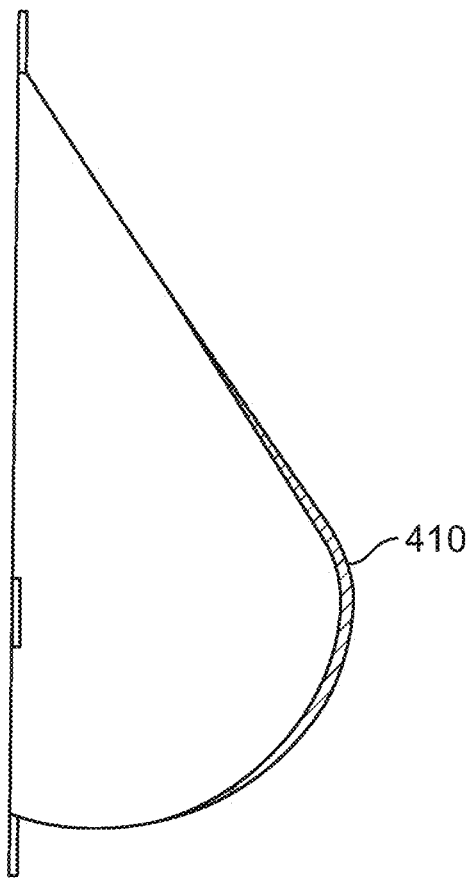
FIGS. 14-15 are diagrams showing left side and front views respectively of another implant including an ancillary layer.
Figure 15:
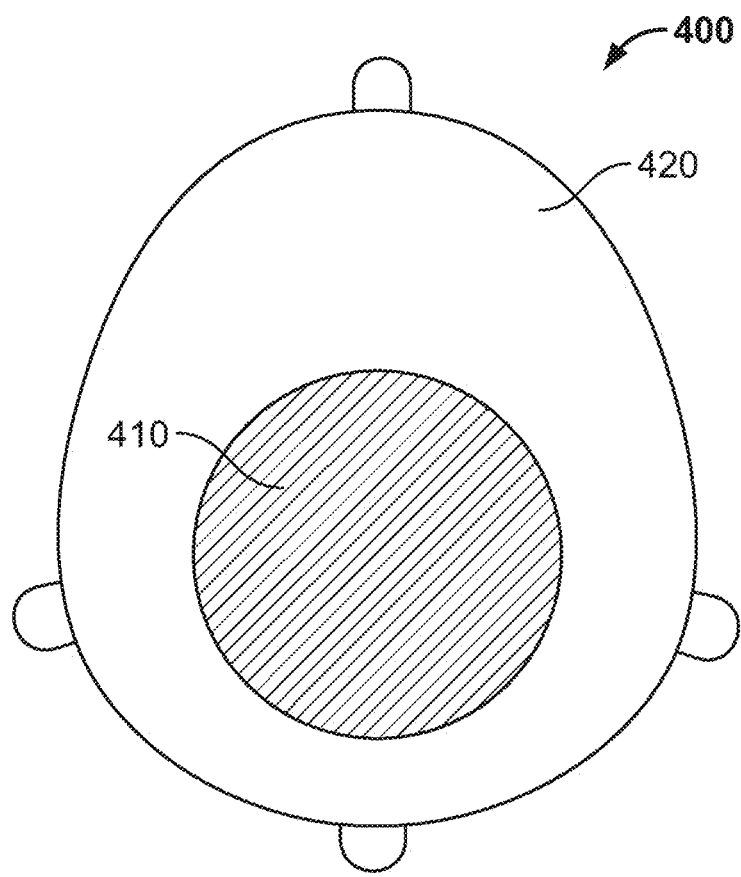

An example of an implant 400 including a redundant layer or second layer 410 is shown in FIGS. 14-15. The second layer may be a biocompatible coating (e.g., collagen type I). The coating 410 is shown covering a first layer or mesh 420 in the area corresponding to the NAC, serving to reduce friction on the skin when the device is implanted underneath the skin. However, the shape and area of the second layer 410 may vary. It may extend and coat the entire first layer 420, or may be smaller and located to cover different areas including, for example, triangular, square or rectangular-shaped discreet regions, etc.

Within the scope described herein, it should be understood that the shapes and dimensions of the implants can vary over certain specific ranges. The implants can be prepared in sizes large enough to allow for their use in mastopexy and breast reconstruction, with or without permanent implants. The implants are wide enough to span the width of a breast.

Figure 7A:
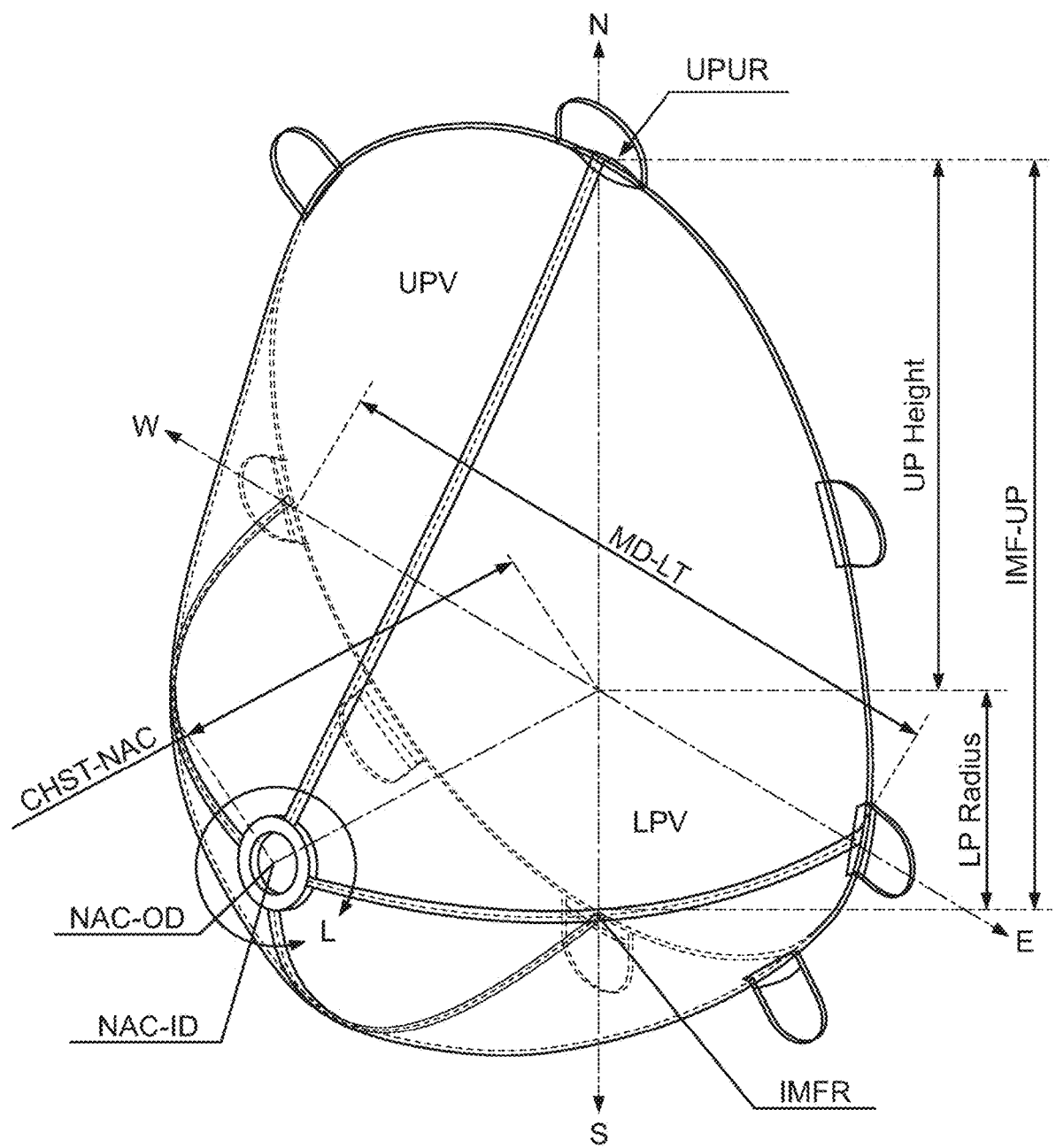
FIG. 7A is a diagram showing an isometric view of a full contour implant in accordance with an embodiment of the invention.

In an embodiment, there are a plurality of sizes (e.g., an implant kit). In an embodiment, there are four sizes and shapes of implant namely, small, medium, large, and x-large. The dimensions of these implants are shown in Table 1, below, wherein IMF-UP is the longitudinal distance between the implant's lowest point, IMFR, (which will be located nearest the IMF of the breast after implantation) and highest point, UPUR, (which will be located nearest the intersection between the breast and chest wall in the upper pole after implantation), MD-LT is the implant width measured from the medial to lateral side of the implant, CHST-NAC is the protrusion distance of the implant from the opening in the implant for the NAC to the intersection of the IMF-UP and MD-LT lines, NAC-ID is the size of the inner diameter of the cutout in the implant that is left open for the patient's NAC, and NAC-OD is the outside diameter of the NAC feature in the implant as shown in FIG. 7A. The distance between the NAC-ID and NAC-OD determines the width of the NAC feature, and the NAC feature's location determines the angulation of the nipple on the breast. The lower pole radius (LP Radius) shown in Table 1, and in FIG. 7A, defines the convex shape of the implant that will be positioned over the lower pole of the breast. The LP Radius is measured from the point of intersection of the IMF-UP and MD-LT lines, to the convex surface of the implant in the region where the implant is designed to cover the lower pole.

TABLE 1

| Dimensions for implants shown in FIG. 7 (excluding tabs) | | | | | | |
|---|---|---|---|---|---|---|
| Size | IMF-UP (cm) | MD-LT (cm) | CHST-NAC (cm) | NAC-ID (cm) | NAC-OD (cm) | LP Radius (cm) |
| Small | 12-14 | 10.8-12.5 | 5-6.4 | 2.5-2.9 | 3-3.4 | 4.2-4.6 |
| Medium | 14-16.2 | 12.5-14.5 | 6.4-7.9 | 2.9-3.5 | 3.4-4 | 5-5.4 |
| Large | 16.2-18.5 | 14.5-16.7 | 7.9-9.6 | 3.5-4.3 | 4-4.8 | 5.8-6.4 |
| X-Large | 18.5-20.8 | 16.7-19.2 | 9.6-11.9 | 4.3-5.3 | 4.8-5.8 | 6.8-7.6 |

Based on the table, the inventors discovered that implants may have an IMF-UP dimension of 12-20.8 cm, a MD-LT dimension of 10.8-19.2 cm, a CHST-NAC dimension of 5-11.9 cm, a NAC-ID dimension of 2.5-5.3 cm, a NAC-OD dimension of 3-5.8 cm, and a LP radius of 4.2-7.6 cm.

The implants may also be defined by the ratio of the LP Radius, to the UP Height shown in FIG. 7A. The UP Height is the distance from the implant's highest point to the intersection of the IMF-UP and MD-LT lines as shown in FIG. 7A. The IMF-UP length is equal to the sum of the lengths of "LP Radius" and "UP Height". In an embodiment, the implant's ratio of UP Height:LP Radius should be 2-2.5:1, and more preferably 2.2:1.

Figure 7B:
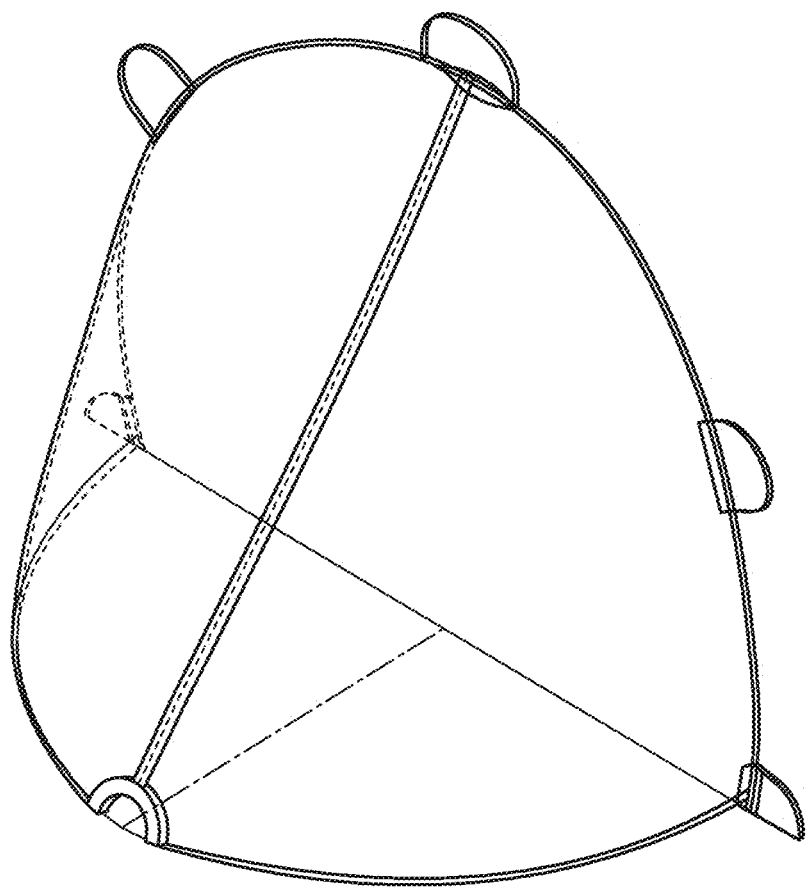
FIGS. 7B-7C are diagrams showing upper and lower pole volumes respectively of the implant shown in FIG. 7A.
Figure 7C:
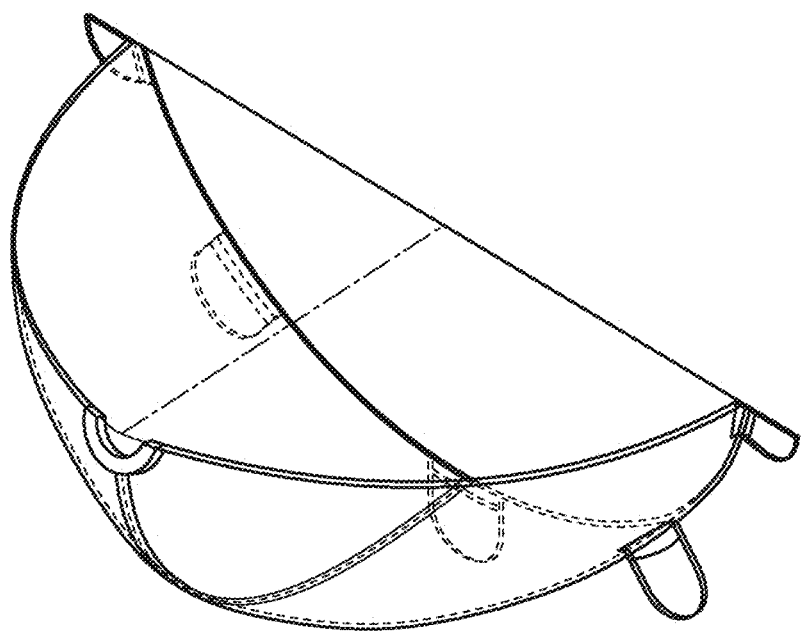

The curvature of the implant that forms the upper pole of the breast may also vary. It may be slightly concave or straight, and is defined by the volumetric ratio of the implant's upper pole to lower pole. This ratio (UPV:LPV of the implant) ranges from 20:80 to 40:60, more preferably 25:75 to 35:65, and even more preferably 28:72. Isometric views of the implant's upper pole volume (UPV) and lower pole volume (LPV) are shown in FIGS. 7B-7C respectively.

In another embodiment, the implant's dimensions are further defined by the protrusion of the implant from the chest wall shown as depth (namely, the distance CHST-NAC in FIG. 7A) and ranges from 5 to 12 cm, or falls within one of the subgroups 4-6; 7-9; and 10-12 cm.

In another embodiment, the implant's dimensions are further defined by (i) the protrusion of the implant from the chest wall shown as CHST-NAC in FIG. 7A, and (ii) the distance from the bottom of the implant to the top of the implant shown as IMF-UP in FIG. 7A.

The implant shapes may have one or more of the following properties (with reference to FIG. 7A): (i) a shape that is filled with 25-35% of the UPV of the breast; (ii) a shape that is filled with 65-75% of the LPV of the breast; (iii) a shape that is filled with a breast volume ratio of UPV:LPV of 28:72; (iv) a cutout positioned in the implant located so that the nipple areola complex can only be positioned at 12 (or 13) to 27 degrees above the NMR line, and more preferably at 18-22 degrees; (v) a convex curvature of the lower pole (LP) radius of the implant; (vi) a straight or slightly concave curvature of the upper pole of the implant between the opening for the NAC and upper pole upper reference point (UPUR) as shown in FIG. 7A; (vii) a ratio of UP Height:LP Radius of 2-2.5:1, and more preferably 2.2:1; (viii) a IMF-UP dimension of 12-20.8 cm, or 10-21 cm (ix) a MD-LT dimension of 10.8-19.2 cm, or 10-20 cm (x) a CHST-NAC dimension of 5-11.9 cm, or 5-12 cm (xi) a NAC-ID dimension of 2.5-5.3 cm, or 2-6 cm (xii) a NAC-OD dimension of 3-5.8 cm, 2.5-6 cm and (xiii) a LP radius of 4.2-7.6 cm or 4-8 cm.

Figure 7D:
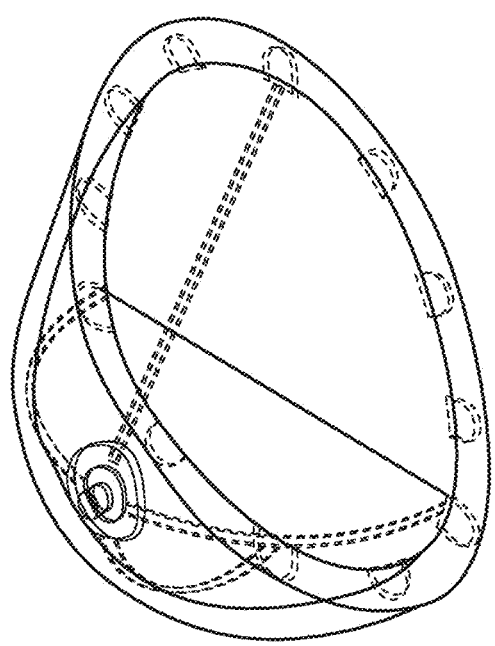
FIGS. 7D-7E are diagrams showing isometric and left profile views respectively of the implant after implantation in a breast.
Figure 7E:
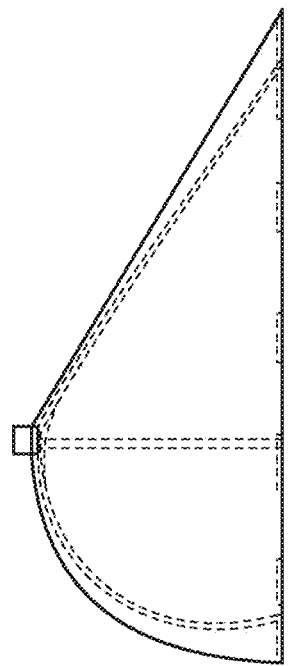

FIGS. 7D-7E show isometric and left profile views, respectively, of the implant after it has been implanted in the breast and overlaid with the patient's skin flap resulting in a reconstructed breast with a UPV of 25-35% and LPV of 65-75%.

The implants disclosed herein may optionally be reinforced, for example, by flexible pillars 120 as shown in FIGS. 6A-6D. The flexible pillars are preferably located on the implant around the NAC, from the NAC to the outer perimeter of the implant, and around the outer perimeter of the implant.

Properties of the Implants

The absorbable implants have been designed to support the mechanical forces acting on the breast during normal activities at the time of implantation, and to allow a steady transition of mechanical forces to regenerated host tissues that can also support those same mechanical forces once the implant has degraded. The implants disclosed herein preferably have burst strengths between 0.6 and 90 N/cm$^2$, more preferably between 1.2 and 30 N/cm$^2$. Preferably, the implant's burst strength 3 months after implantation is at least 40% of its initial burst strength.

The implants are preferably porous, and can be replaced in vivo by host tissue growing into and around the implant that is strong enough to support the breast. The diameters of the implant's pores are preferably larger than 25 μm, more preferably larger than 75 μm, and even more preferably larger than 250 μm in order to facilitate tissue in-growth, but smaller than 10 mm, more preferably smaller than 5 mm, and even more preferably smaller than 2 mm. Non-limiting examples of porous constructs that can be used to make the implant include mesh construct, fabric construct, woven construct, non-woven construct, knitted construct, braided construct, porous film construct including laminated and perforated film construct, nanospun construct, electrospun construct, or melt-blown construct, and combinations thereof, as well as thermoforms of these constructs. Preferably, these constructs are made from P4HB, and even more preferably from oriented, partially oriented, or unoriented P4HB monofilament textiles.

The implant can be designed so that it stretches equally in each direction. The implant may also be designed so that it may stretch more in some directions than in other directions. The ability of the implant to stretch can allow the surgeon to place tension on the breast during implantation. However, in order to maintain support for the breast following surgery, it is important that after the implant is implanted, the implant, the regenerated host tissue, and any transitional structures, cannot stretch significantly. In an embodiment, the implant cannot stretch more than 30% of its original length in any direction. In an even more preferred embodiment, the implants cannot stretch more than 20% of their original length in any direction and comprise fibers of poly-4-hydroxybutryate or copolymer thereof with elongation to break values of 25-95%, more preferably 25-55%.

In one embodiment, the implants can be temporarily deformed and resume their original three-dimensional preformed shapes after implantation into a suitably dissected tissue plane.

In a particularly preferred embodiment, the full contour implants are sutured in place. Without intending to being bound to theory, the load exerted by the breast is spread out over the implant, the entire force of the breast tissue is shared among the points of attachment of the implant to the body. An advantage of the absorbable implants disclosed herein is that they possess a high suture pullout strength that allows a heavy breast to be supported with a limited number of anchoring sites. In a preferred embodiment, an implant is anchored to the chest wall at four or more places, preferably 4-12 places, in order to support the breast. This strategy distributes the load over multiple attachment points. In a particularly preferred embodiment, the implant has tabs with high suture pullout strengths, preferably 2-20 tabs, more preferably 4-12 tabs, that are located around the edges of the implant to allow suturing of the implant to the tissue surrounding the breast glandular tissue. The dimensions of the tabs are preferably from 0.5 cm×0.5 cm to 5 cm×4 cm, preferably 2 cm×2.5 cm. The implant and any tabs must have sufficient strength retention in vivo to resist mechanical loads while tissue in-growth occurs. In a particularly preferred embodiment, the suture pullout strength of the absorbable implant, and any tabs attached thereto, is greater than 10 N, and more preferably greater than 20 N. In one embodiment, these suture pullout strengths can be obtained if the implants, and any tabs attached thereto, comprise oriented P4HB monofilament fibers, more preferably knitted oriented P4HB monofilament fibers, and even more preferably oriented P4HB monofilament fibers that have been formed into a textile structure.

In an embodiment, the three-dimensional implant has properties that allow it to be delivered through a small incision. The implant may, for example, be designed so that it can be rolled or folded to allow delivery through a small incision. This minimally invasive approach can reduce patient morbidity, scarring and the chance of infection. In an even more preferred embodiment, the implant has a three-dimensional shape and shape memory properties that allow it to assume its original three-dimensional shape unaided after it has been delivered through an incision and into an appropriately sized dissected tissue plane. For example, the implant may be temporarily deformed by rolling it up into a small diameter cylindrical shape, delivered using an inserter, and then allowed to resume its original three-dimensional shape unaided in vivo. Flexible pillars, such as those shown in FIG. 6, may be incorporated into the implant in order to facilitate implantation, and to allow the implant to regain shape more easily after implantation. The pillars preferably have diameters or widths ranging from 0.5 to 3 mm, and are preferably made from unoriented, partially or fully oriented P4HB polymer or copolymer thereof.

Construction of the Implants

A variety of methods can be used to manufacture the implants, and their scaffold structures.

In a particularly preferred embodiment, the implants are prepared by molding a porous construct into a three-dimensional shape using a mold that has the shape of a breast and specific volumetric ratios in the upper and lower parts of the mold. The volumetric ratios of the mold are selected to produce an implant that will redistribute the tissues of the breast so that the volume occupied by the upper pole of the breast is 25-35% of the total volume, and the volume occupied by the lower pole of the breast is 65-75% of the total volume. More preferably the implant redistributes the breast volume so the upper pole to lower pole volumetric ratio is 28:72.

Figure 8A:
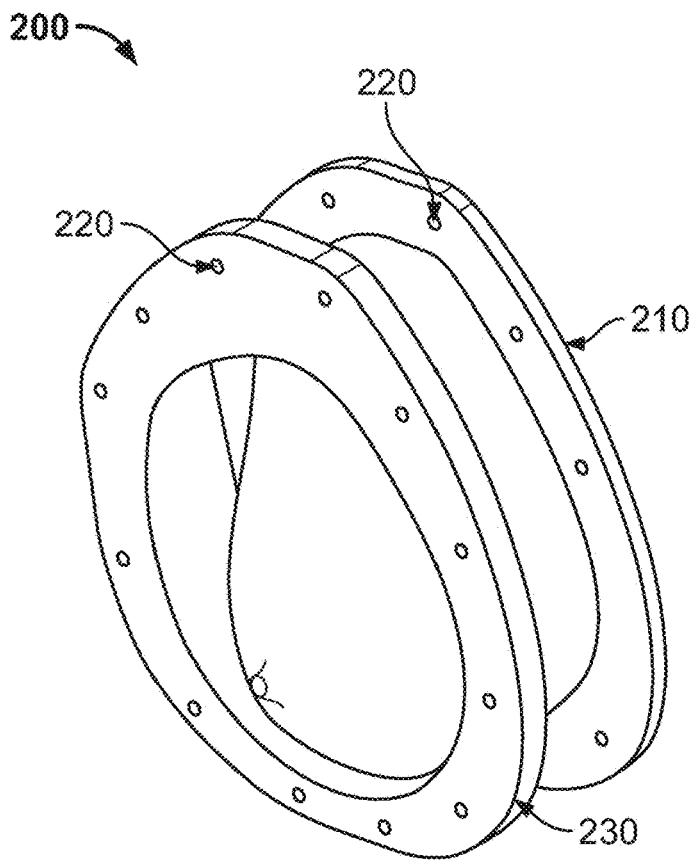
FIG. 8A is a diagram showing an isometric view of an example of a three-dimensional mold that can be used to manufacture a full contour breast implant.

An example of a mold 200 with these volumetric ratios is shown in FIG. 8A. In addition to having specific volumetric ratios, the mold is shaped to have a convex curvature in the lower pole and a straight to slightly concave curvature in the upper pole. For illustration purposes, the position of a nipple is shown on the mold. The mold is designed to produce an implant where the location of the nipple, after implantation of the implant, will be between 12 (or 13) and 27 degrees above the nipple meridian reference (NMR) line of the breast, more preferably between 18 and 22 degrees above the NMR line. After molding, the area around the nipple of the implant is cutout so the patient's NAC may protrude through the opening upon implantation.

The mold shown in FIG. 8A has an outer flat edge 210 with holes 220 that allow connection to a pressure ring 230 (also shown in FIG. 8A). A porous construct 240, such as a two-dimensional mesh, preferably a monofilament mesh, may be inserted in the mold as shown in the cross-sectional diagram in FIG. 8B, and held under tension by an O-ring present in a groove in the pressure ring. When the pressure ring is clamped to the breast shaped plate, the O-ring presses on the porous construct to keep it from moving, and prevents the porous construct from shrinking during molding. To impart the desired implant shape to the porous construct, the non-porous construct 240 held under tension in the mold assembly may be thermoformed, and then removed from the mold. In a preferred embodiment, an oriented P4HB monofilament mesh is thermoformed by placing the assembly of the mold and mesh in hot water, and then quenching the mesh by placing the assembly of the mold and mesh in cold water. The oriented P4HB monofilament mesh preferably has an areal density of 5 to 800 $g/m^2$. In a particularly preferred embodiment, the assembly containing the P4HB monofilament mesh is placed in hot water where the temperature is 55-63° C., more preferably 56-58° C., for 3-10 minutes, more preferably 3-5 minutes, and then quenched in cold water where the temperature is 2-12° C., more preferably 6-10° C., for 2-15 minutes, more preferably 5-10 minutes.

Figure 9:
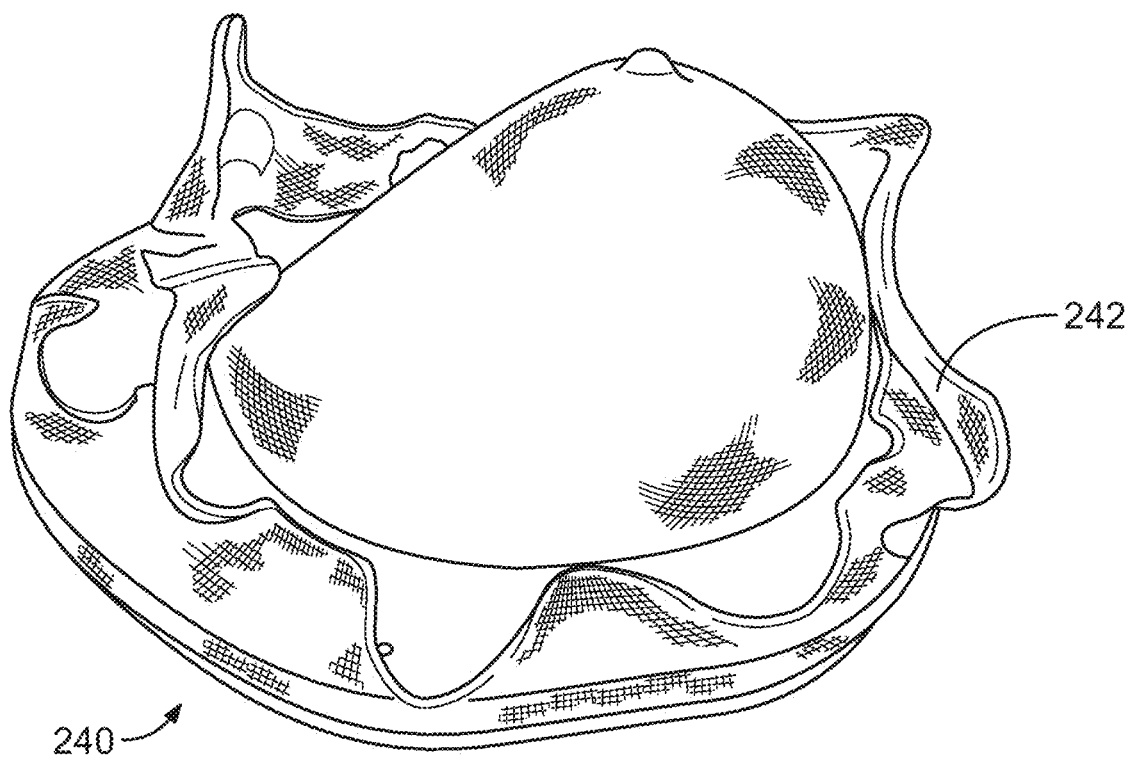
FIG. 9 depicts a mesh implant fastened in a mold with excess mesh visible around the outside edge of the mold.
Figure 10:
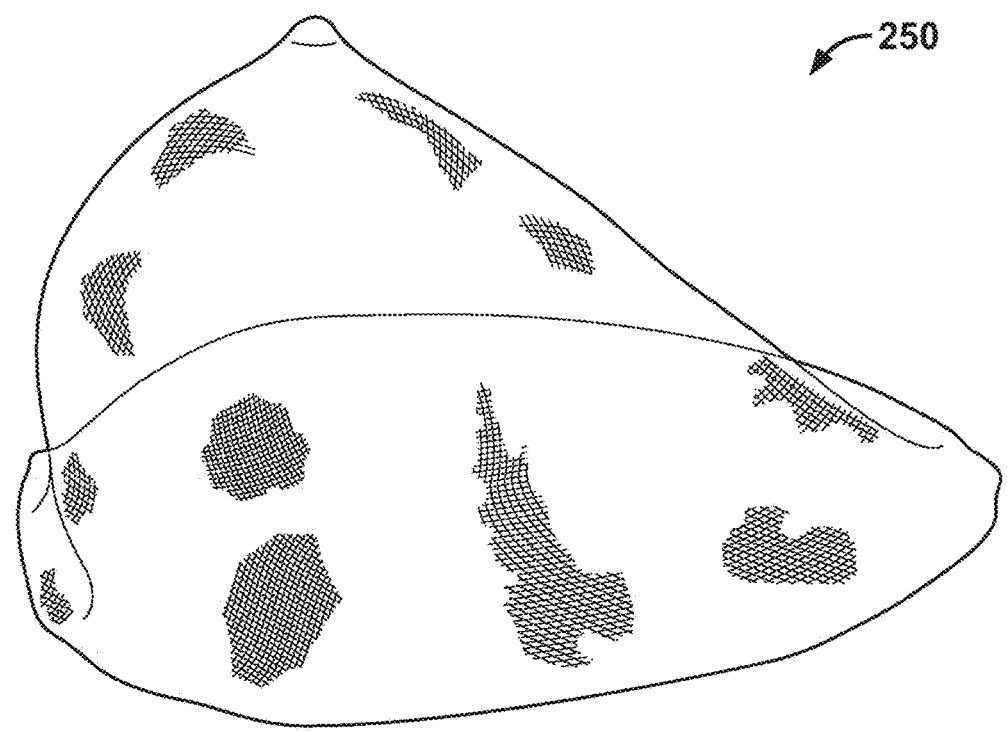
FIG. 10 depicts a full contour implant made in accordance with an embodiment of the invention.

FIG. 9 shows a porous construct 240 on a mold that has been thermoformed using the mold shown in FIG. 8A. In this example, the porous construct is a P4HB mesh made from oriented P4HB monofilament fibers. FIG. 9 shows the molded P4HB mesh in the mold with excess material 242 around the edge of the mold. This excess material may be removed by trimming, for example, to form the implant 250 shown in FIG. 10.

Figure 11:
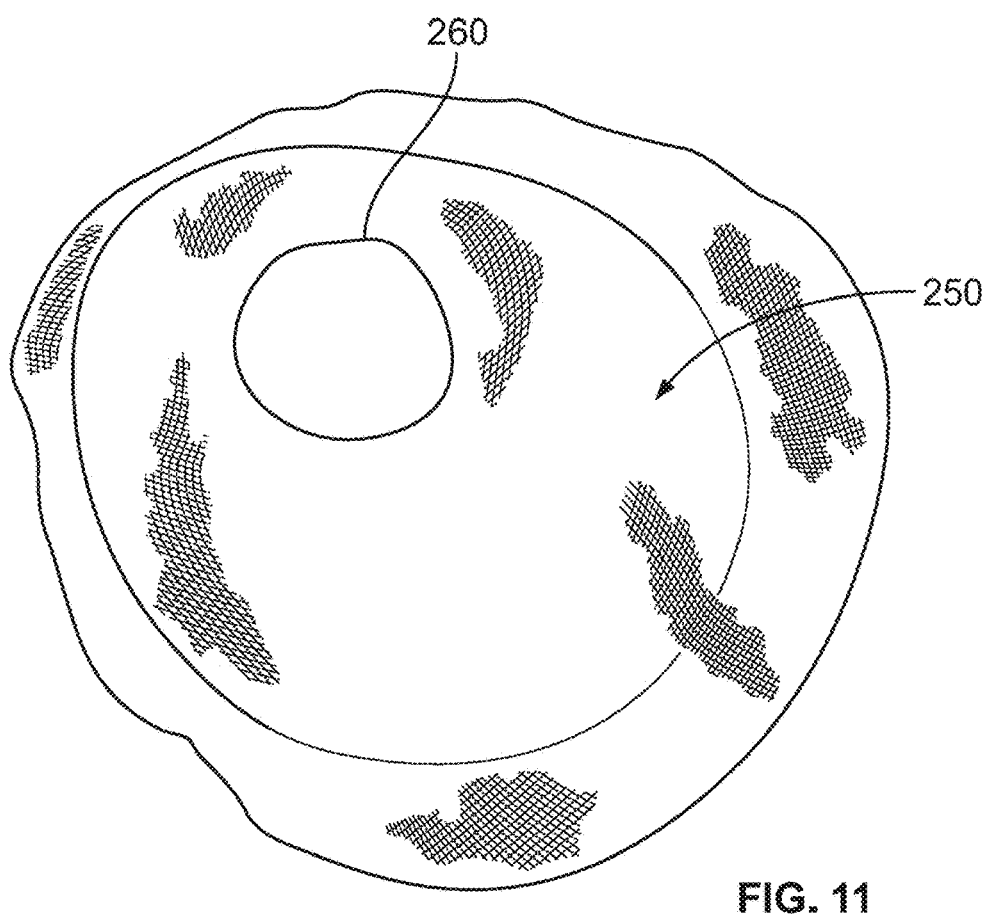
FIG. 11 depicts another full contour implant including an opening to receive the patient's NAC.

FIG. 11 shows a hole 260 cut in the implant of FIG. 9 to accommodate the patient's NAC.

Figure 12:
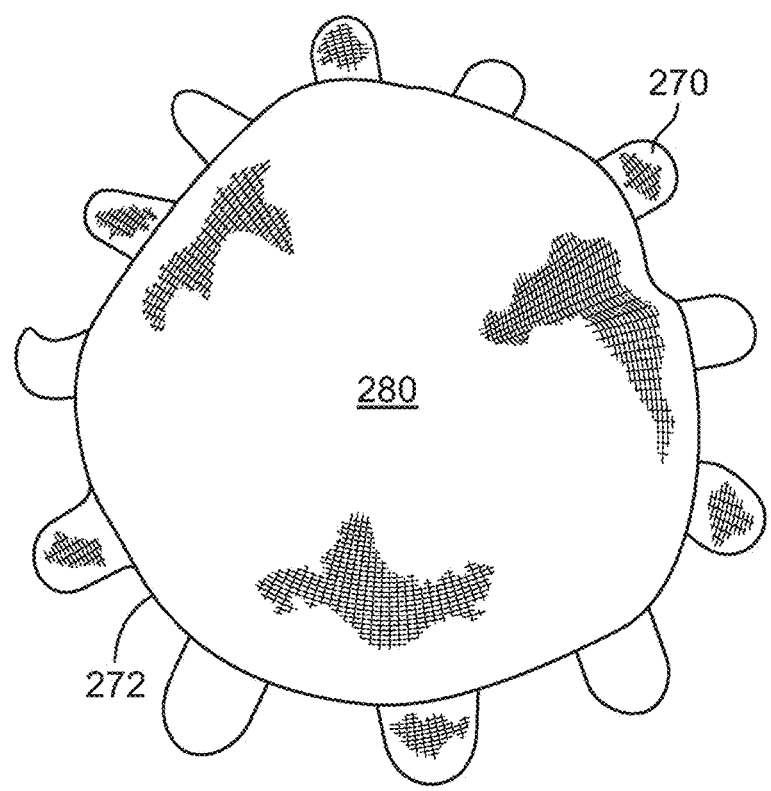
FIG. 12 depicts another full contour implant including a plurality tabs extending from its outer edge.

With reference to FIG. 12, a mesh 280 is shown having tabs 270 around the perimeter 272 of the mesh. The tabs may be formed by trimming around the perimeter of the mesh described above. The number of tabs may vary. In embodiments, there are 1, 2, 3, 4, 5, 6, 7, 8, 9, 10, 11, 12, 13, 14, 15, 16, 17, 18, 19, 20 tabs or more, but preferably 4-12. FIG. 12 shows an implant 280 with 12 tabs.

The porous construct molded as described above may optionally further comprise guiding flexible pillars. A diagram of an implant comprising guiding flexible pillars is shown in FIG. 6A. In this example, the guiding flexible pillars run in straight direct lines between the NAC and the outer edge of the implant over the outer surface of the implant. FIG. 6A shows four guiding flexible pillars connecting the NAC to the outer edges of the implant. However, the number of guiding pillars may vary and may be 1, 2, 3, 4, 5, 6, 7, 8, 9, 10, 11, 12 or more, but preferably 4-12. The flexible guiding pillars may be incorporated into the implants by any suitable method, including fusion, molding, knitting or printing either before or after molding. In one embodiment, the flexible guiding pillars are incorporated by fusing absorbable polymeric fibers to the implant. Preferably, unoriented fiber extrudate is fused to the implants. In a particularly preferred embodiment, unoriented P4HB fiber extrudate may be fused to the implant, preferably an implant also made from P4HB, particularly a P4HB monofilament mesh. In another embodiment, flexible guiding pillars may be printed directly onto the porous construct before molding, or after molding. Preferably an absorbable thermoplastic, such as P4HB, is printed.

In another embodiment, the cutout or aperture 110 in the implant for receiving the patient's NAC may be further modified as indicated by the "NAC Feature" shown in FIG. 6A. This can be particularly desirable if the edges of the cutout are sharp or rough. For example, cutting out a hole from a monofilament mesh to receive the patient's NAC will result in a non-smooth edge that could irritate surrounding tissues upon implantation. A smoother opening for the NAC can be made, for example, by fusing a fiber 112 around the circumference of the cutout so the sharp ends of the cutout are smoothly sealed, or printing an absorbable thermoplastic on the sharp ends. In a preferred embodiment, a P4HB fiber extrudate is fused around the circumference of the cutout to form a "NAC Feature". Even more preferably, the P4HB fiber extrudate is fused around the circumference of an NAC cutout in an implant made from P4HB monofilament mesh.

Other porous constructs, besides monofilament meshes, may be molded to form the implants. For example, the porous constructs may comprise multifilament fibers, or combinations of monofilament and multifilament fibers. These porous constructs may be woven or knitted. The porous constructs may be produced by either warp or weft knitting processes, however, a warp knit is preferred in order to minimize the stretching of the implant. A P4HB warp knitted mesh made from oriented P4HB monofilament fiber is particularly preferred.

The porous construct for molding into the implants may alternatively comprise perforated films (oriented or unoriented), non-wovens, laminates, electrospun fabric, solvent and melt spun fabric, foam, thermally bonded fibers, wet or solution spun fibers, dry spun fibers, thermoforms, or other porous materials. The porous construct may also be prepared by a process that uses particulate leaching, preferably wherein the leachable particle materials have a diameter of at least 50 μm, more preferably at least 75 μm, but less than 5 or 10 mm. Alternatively, the porous constructs may be prepared by phase separation. The porous construct may be a combination of two or more materials.

The processes described herein to produce the implants can also be used in combination. For example, a woven construct could be combined with a non-woven construct, and molded to form an implant. Or, an implant could be prepared by printing on a mesh.

In still another embodiment, the implants may be prepared by methods that include 3D printing (also known as additive manufacturing). This method is particularly useful in the manufacture of specific shapes since the desired shape can be made directly without the need for further cutting or trimming. In a preferred embodiment, the implant is made by 3D printing with P4HB, more preferably 3D printing in combination with a mold.

In another embodiment, the implants comprise retainers, such as barbs or tacks, so that the implant can be anchored to the chest wall in certain places without the use of sutures. For example, the three-dimensional implants may contain retainers in their outlying borders to anchor the implants.

The implants can be trimmed or cut with scissors, blades, other sharp cutting instruments, or thermal knives in order to provide the desired implant shapes. The implants can also be cut into the desired shapes using laser-cutting techniques. This can be particularly advantageous in shaping fiber-based implants because the technique is versatile, and importantly can provide shaped products with sealed edges that do not shed cut loops or debris produced in the cutting process.

Methods for Implanting the Full Contour Breast Implants

The implants described herein are most suited for use in breast surgery, and more particularly for mastopexy or mastopexy augmentation procedures. However, the implants may also be used in other procedures such as revision procedures following the removal of a breast implant, and breast reconstruction procedures following mastectomy, particularly where it is desirable to retain the position of a silicone or saline breast implant.

In an embodiment, a method of implantation of the implants comprises at least the steps of: (i) making at least one incision to gain access to the breast tissue of the patient, (ii) separating the skin and subcutaneous fascia from the breast mound of the breast, (iii) positioning the implant on the breast mound of the breast so that the NAC protrudes through the opening for the NAC in the implant (and the implant is oriented so that the convex curvature of the implant contacts the lower pole of the breast tissue, the straight or slightly concave curvature of the implant contacts the upper pole of the breast tissue, and the nipple is angulated in a slightly skyward direction), (iv) securing the implant to the tissue surrounding the breast mound of the breast, and (v) closing the incisions in the breast.

In one embodiment, the breast may be prepared for receiving the implant by making a Wise-type or inverted T-type incision. In this procedure, incisions are made around the areolar complex, vertically in the lower pole of the breast from the IMF to the areolar complex, and along the inframammary fold to form an inverted T-pattern. In a variation of this procedure, two vertical incisions may be made in the lower pole of the breast to increase access to the underlying breast tissue. This procedure may also be employed when it is desirable to remove excess skin from the lower breast. The skin between the two incisions may be removed, and at the end of the procedure the two incisions may be joined, for example, by suturing.

In an alternative surgical approach, the breast can be prepared for the implant using a less invasive procedure. This is accomplished by making an incision around the areolar (a peri-areolar incision), and then exposing the breast tissue by pulling the skin away from the areolar. The advantage of this approach is that scarring of the skin is minimized, and the areolar structure is not damaged.

The breast may also be prepared to receive the implant using a lollipop procedure wherein an incision is made around the areolar (a peri-areolar incision), and a vertical incision is made in the lower pole from the areolar complex to the inframammary fold.

Once the T-type, peri-areolar or lollipop incisions have been made, the surgeon may prepare the breast to receive the implant by separating the skin and subcutaneous fascia from the breast mound of the breast. Dissection is performed in the subcutaneous plane around the breast superior to the subclavicular, sterno-clavicular and anterior axillary regions and medially to the parasternal region as well as laterally to the anterior axillary line in a manner that provides an adequate flap thickness. After dissection is complete, the surgeon selects the correctly sized implant. The surgeon can optionally use transparent sterile sizing guides (e.g. shapes molded in the same size as the implants with cutouts for the NAC) to assist with this process by inserting these guides into the exposed breast between the breast mound and the skin until the desired size is identified. If a guide is too small, it will not be possible to locate all the breast tissue underneath it, and therefore an implant of the same size would be too small. If the guide is too large, the underlying breast tissue will be free to move about and will not be proportioned in the desired volumetric ratios for the upper and lower poles. Once the guide with the optimum dimensions is identified, the correctly sized implant can be selected and inserted into the breast. The implant is inserted into the breast under the skin and positioned to cover the exposed breast mound by pulling the skin away to the extent necessary. The surgeon may manipulate the implant by hand to make sure it is correctly positioned, and also to make sure there are no wrinkles in the implant. Optionally, the surgeon may also temporarily insert a transparent molded guide on top of the implant to smooth the placement of the implant on the breast tissue, and if desired, to hold the implant in place while it is fixated. Once the implant has been located in the desired position, it may be secured in place, for example, by suturing the implant to the tissue surrounding the breast mound. The implant is preferably sutured to the fascia surrounding the pectoral muscle underlying the breast mound.

In a particularly desired embodiment, the implant comprises one or more tabs as shown in FIGS. 6A and 12 that can be sutured to the tissue surrounding the breast mound. The implant may have 1, 2, 3, 4, 5, 6, 7, 8, 9, 10, 11, 12, 13, 14, 15, 16, 17, 18, 19, 20 or more tabs that can be used to secure the implant in place, but preferably 4-12 tabs.

Once the implant has been fixated, the breast can be closed by suturing the incision lines closed. In embodiments, an implant is fixated in both breasts. After the procedure is completed in one or both breasts, and the patient is standing upright, the total breast volume will be distributed so that the tissue volume in the upper pole of each breast is 25-35%, and the tissue volume in the lower pole of each breast is 65-75%. The patient's lower poles will have a convex shape, and the upper poles will have a straight or slightly concave shape. Furthermore, the patient's nipples will be pointing slightly skyward angulated between 12 (or 13) and 27% above the nipple median reference (NMR) line. Inventors have discovered that, amongst other things, controlling the depth of the implant (namely, the distance CHST-NAC or projection line) serves to support the breast in a desired shape.

In another embodiment, the procedures described above can be performed with breast implant augmentation. For example, a permanent breast implant may be implanted to increase breast volume. The permanent breast implant may, for example, be a silicone or saline implant.

In a further embodiment, the procedures described above can be performed with removal of breast tissue, resection and redistribution of breast tissue.

The present invention will be further understood by reference to the following non-limiting examples.

Example 1: Preparation of a Full Contour Absorbable Breast Implant

A full contour breast implant was prepared from a P4HB monofilament mesh with a MARLEX® knit pattern that was derived from a size 5-0 oriented P4HB monofilament fiber with an elongation to break of 25%, and a weight average molecular weight of 350 kDa. The mesh was scoured after knitting to remove textile processing aids, and then cut into oval pieces that were 50% larger than the base of the 3D breast-shaped mold show in FIG. 8A. Prior to molding the mesh into the three-dimensional shape, P4HB unoriented extrudate with a diameter of 0.8-1.2 mm, was fused to the mesh to form guiding flexible pillars and a NAC feature so that after molding these features would have the positions shown in FIG. 6. The P4HB unoriented extrudate was fused to the mesh using two flat molds that applied tension to the mesh. The molds were heated to 57° C. for 5 minutes, and then the assembly of the mold and mesh was quenched at 9° C. for 10 mins before dismantling the mold.

Figure 8B:
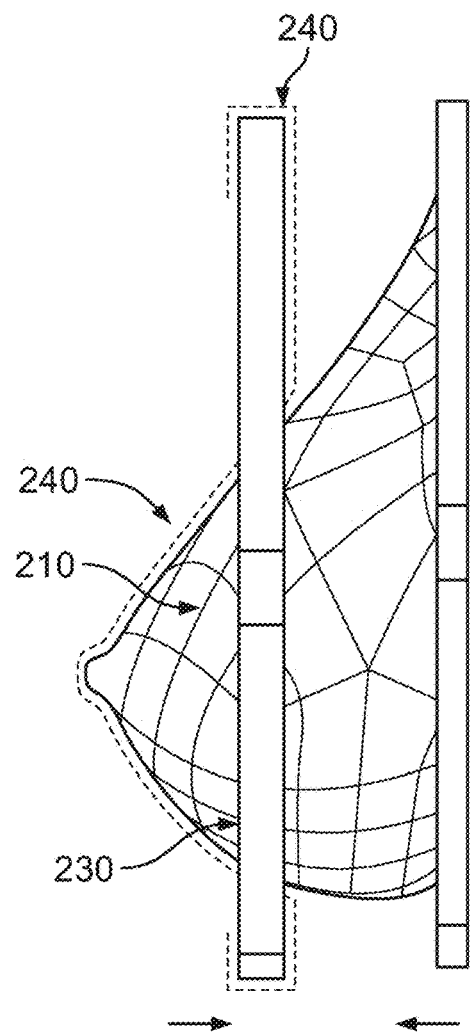
FIG. 8B is a diagram showing a cross-sectional view of a mesh positioned in the mold shown in FIG. 8A for thermoforming into a full contour breast implant in accordance with an embodiment of the invention.
Figure 13:
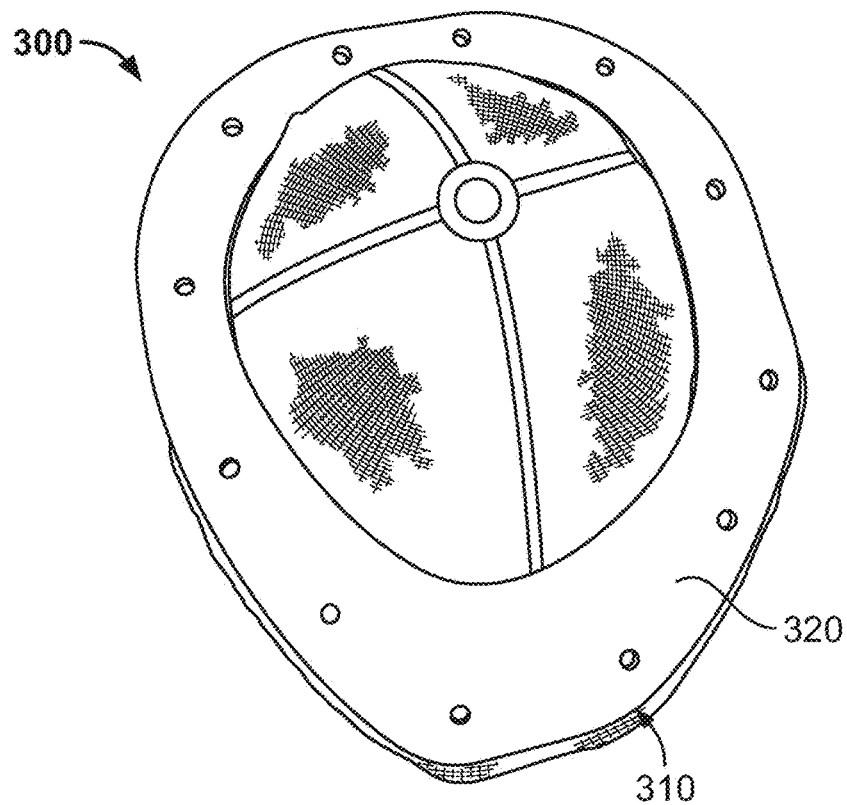
FIG. 13 depicts another full contour implant held in a mold.

To impart a precise three-dimensional shape to the implant with specific volumetric ratios of the lower and upper poles, the three-dimensional mold shown in FIG. 8A was used. The mold shown in FIG. 8A is shaped such that the breast volume will be distributed in the patient so that the upper pole volume (UPV) is between 25-35%, and the lower pole volume (LPV) is between 65-75%, of the total breast volume, and wherein the mold will produce a three-dimensional shape that angulates the patient's nipple between 12 (or 13) and 27% above the nipple median reference (NMVR) line. The P4HB mesh with unoriented extrudate attached as described above was placed over the mold shown in FIG. 8B, and fastened under tension using the pressure ring shown in FIG. 8B. It is important to apply tension on the mesh to prevent shrinkage of the mesh during molding. Tension is applied on the mesh by contact with an inner O-ring that sits in a groove in the pressure ring 230 as indicated in FIG. 8B. The pressure ring can be fastened to the mold using clamps. Once the assembly of the mold was completed, the assembly was placed in hot water heated to 57° C. for 5 minutes, and then quenched in a cold-water bath with a temperature of 9° C. for 10 minutes to form the three-dimensional implant shape. After quenching, the assembly with excess mesh visible around the outside edge of the mold was removed from the cold-water bath. To complete the preparation of the implant, the clamps are released, the mold disassembled, excess mesh trimmed from the implant, and the NAC opening made using a round die cutter and press. The resulting implant 300 is shown in FIG. 13 with the outer edge 310 covered by the pressure ring 320. Optionally, the mesh may be trimmed so that the implant comprises one or more attachment tabs as shown in FIG. 6. These tabs can be used by the surgeon during implantation to orient and fixate the implant at specific locations.

Similar implants may be prepared using (i) P4HB monofilament with elongation to break values of 25-95%, preferably 55-95%, (ii) P4HB polymer weight average molecular weights of 250-600 kDa, (iii) P4HB unoriented extrudate with diameters ranging from 0.5-2 mm, (iv) molding of the P4HB mesh in hot water with a temperature of 55-63° C. for 3-10 minutes, and (v) quenching of the P4HB mesh in cold water with a temperature of 2-12° C. for 2-15 minutes.

Modifications and variations of the methods and compositions will be apparent from the foregoing detailed description and are intended to come within the scope of the appended claims.

We claim:

1. A method of manufacturing an implant comprising the steps of: (i) preparing a three-dimensional mold in the shape of an implant, (ii) molding a porous two-dimensional construct into a three-dimensional shape using the three-dimensional mold, (iii) removing the molded shape from the mold, (iv) cutting an aperture in the molded three-dimensional shape in a position to angulate the patient's nipple areola complex (NAC) slightly skyward so that the angle between the nipple projection line and the nipple meridian reference line is 1-27 degrees after implantation, and (v) connecting the mold to a pressure ring.

2. The method of claim 1, further comprising (vi) trimming an edge of the implant to add one or more tabs to the implant.

3. The method of claim 1, further comprising molding a first flexible pillar around the circumference of the aperture to form a NAC feature.

4. The method of claim 1, wherein the porous two-dimensional construct is a monofilament mesh.

5. The method of claim 1, further comprising molding a plurality of reinforcing pillars radially extending from the aperture to an outer edge of the implant.

6. The method of claim 1, wherein a volume occupied by an upper pole of the patient's breast is 25-35% of a total volume of the molded three-dimensional shape.

7. The method of claim 1, wherein the implant is shaped to redistribute the patient's breast volume so that an upper pole to lower pole volumetric ratio is 28:72.

8. The method of claim 1, wherein the mold comprises an outer flat edge with a plurality of holes.

9. The method of claim 1, wherein the step of molding the porous two-dimensional construct comprises inserting the porous two-dimensional construct in the mold and holding the porous two-dimensional construct under tension.

10. The method of claim 9, wherein the porous two-dimensional construct is held under tension by an O-ring.

11. The method of claim 10, wherein the O-ring is present in a groove in a pressure ring.

12. The method of claim 1, further comprising placing the mold in hot water during step (ii).

13. The method of claim 1, further comprising quenching the mold during step (ii).

14. The method of claim 1, further comprising fusing unoriented fiber extrudate to the implant.

15. The method of claim 1, further comprising fusing a fiber around a circumference of the aperture.

16. The method of claim 15, wherein the fiber comprises a poly-4-hydroxybutyrate (P4HB) fiber extrudate.

17. The method of claim 1, further comprising printing an absorbable thermoplastic on at least a portion of a circumference of the aperture.

18. The method of claim 1, wherein the implant is absorbable.

19. The method of claim 1, further comprising quenching the mold during step (ii).

20. A method of manufacturing an implant comprising the steps of: (i) preparing a three-dimensional mold in the shape of an implant, (ii) molding a porous two-dimensional construct into a three-dimensional shape using the three-dimensional mold, (iii) removing the molded shape from the mold, (iv) cutting an aperture in the molded three-dimensional shape in a position to angulate the patient's nipple areola complex (NAC) slightly skyward so that the angle between the nipple projection line and the nipple meridian reference line is 1-27 degrees after implantation, and (v) molding a plurality of reinforcing pillars radially extending from the aperture to an outer edge of the implant.

21. The method of claim 20, further comprising (vi) trimming an edge of the implant to add one or more tabs to the implant.

22. The method of claim 20, further comprising molding a first flexible pillar around the circumference of the aperture to form a NAC feature.

23. The method of claim 20, wherein a volume occupied by an upper pole of the patient's breast is 25-35% of a total volume of the molded three-dimensional shape.

24. The method of claim 20, wherein the implant is absorbable.

25. A method of manufacturing an implant comprising the steps of: (i) preparing a three-dimensional mold in the shape of an implant, (ii) molding a porous two-dimensional construct into a three-dimensional shape using the three-dimensional mold, (iii) removing the molded shape from the mold, (iv) cutting an aperture in the molded three-dimensional shape in a position to angulate the patient's nipple areola complex (NAC) slightly skyward so that the angle between the nipple projection line and the nipple meridian reference line is 1-27 degrees after implantation, wherein a volume occupied by an upper pole of the patient's breast is 25-35% of a total volume of the molded three-dimensional shape.

26. A method of manufacturing an implant comprising the steps of: (i) preparing a three-dimensional mold in the shape of an implant, (ii) molding a porous two-dimensional construct into a three-dimensional shape using the three-dimensional mold by inserting the porous two-dimensional construct in the mold and holding the porous two-dimensional construct under tension by an O-ring, (iii) removing the molded shape from the mold, (iv) cutting an aperture in the molded three-dimensional shape in a position to angulate the patient's nipple areola complex (NAC) slightly skyward so that the angle between the nipple projection line and the nipple meridian reference line is 1-27 degrees after implantation.

27. The method of claim 26, further comprising molding a plurality of reinforcing pillars radially extending from the aperture to an outer edge of the implant.

28. The method of claim 26, wherein a volume occupied by an upper pole of the patient's breast is 25-35% of a total volume of the molded three-dimensional shape.

29. The method of claim 26, further comprising connecting the mold to a pressure ring.

30. The method of claim 26, wherein the O-ring is present in a groove in a pressure ring.

\* \* \* \* \*